United States Patent
Bucher et al.

(10) Patent No.: US 12,428,393 B2
(45) Date of Patent: Sep. 30, 2025

(54) METHODS OF MAKING TRANS ISOMERIC FORMS OF G PROTEIN-COUPLED RECEPTOR MODULATORS

(71) Applicant: RAPT THERAPEUTICS, INC., South San Francisco, CA (US)

(72) Inventors: Cyril Bucher, San Mateo, CA (US); James P. Davidson, South San Francisco, CA (US); Jeffrey J. Jackson, San Bruno, CA (US); Michelle Yoo Min Ko, San Francisco, CA (US); Grant Shibuya, South San Francisco, CA (US); David J. Wustrow, South San Francisco, CA (US); Ashkaan Younai, Daly City, CA (US); Mikhail Zibinsky, Redwood City, CA (US)

(73) Assignee: RAPT THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/588,173

(22) Filed: Jan. 28, 2022

(65) Prior Publication Data

US 2022/0251070 A1    Aug. 11, 2022

Related U.S. Application Data

(60) Provisional application No. 63/144,878, filed on Feb. 2, 2021.

(51) Int. Cl.
*C07D 401/14*    (2006.01)
*C07D 401/04*    (2006.01)
*C07D 495/04*    (2006.01)

(52) U.S. Cl.
CPC ......... *C07D 401/14* (2013.01); *C07D 401/04* (2013.01); *C07D 495/04* (2013.01)

(58) Field of Classification Search
CPC .................................................. C07D 401/04
See application file for complete search history.

(56) References Cited

U.S. PATENT DOCUMENTS 10,683,280 B2    6/2020   Jackson et al.
2019/0233397 A1*  8/2019   Jackson ............... A61P 35/00

FOREIGN PATENT DOCUMENTS

WO    WO-2019147862 A1 *  8/2019    ........... A61K 31/506

OTHER PUBLICATIONS

Horuk, R. (May 1994. "Molecular properties of the chemokine receptor family," *Trends Pharm. Sci.* 15:159-165.
International Search Report mailed on Apr. 25, 2022, for PCT Application No. PCT/US2022/014450, filed Jan. 28, 2022, 8 pages.
Munson, P.J. et al. (Sep. 1, 1980). "Ligand: a versatile computerized approach for characterization of ligand-binding systems," *Analyt. Biochem.* 107(1):220-239.
Ouellet, S.G. et al. (Dec. 2007). "Enantioselective organocatalytic transfer hydrogenation reactions using Hantzsch esters," *Acc Chem Res* 40(12):1327-1339.
Tripathi, R.P. et al. (2008). "Recent Development on Catalytic Reductive Amination and Applications," *Current Organic Chemistry* 12:1093-1115.
Wakchaure, V.N. et al. (2010). "Towards a Practical Bronsted Acid Catalyzed and Hantzsch Ester Mediated Asymmetric Reductive Amination of Ketones with Benzylamine," *Synlett* 2010(18):2708-2710.
Wang, P-Z. et al. (Aug. 7, 2019, e-published Jul. 3, 2019). "Hantzsch esters: an emerging versatile class of reagents in photoredox catalyzed organic synthesis," *Org. Biomol. Chem.* 17(29):6936-6951.
Written Opinion mailed on Apr. 25, 2022, for PCT Application No. PCT/US2022/014450, filed Jan. 28, 2022, 11 pages.
Zheng, C. et al. (Mar. 21, 2012, e-published Jan. 27, 2012 "Transfer hydrogenation with Hantzsch esters and related organic hydride donors," *Chem Soc Rev* 41(6):2498-2518.
Zhu, C. et al. (Sep. 17, 2009). "Benzothiazoline: highly efficient reducing agent for the enantioselective organocatalytic transfer hydrogenation of ketimines," *Organic Letters* 11(18):4180-4183.

* cited by examiner

*Primary Examiner* — Jeffrey S Lundgren
*Assistant Examiner* — Eric Tran
(74) *Attorney, Agent, or Firm* — Irina E. Britva; Mintz, Levin, Cohn, Ferris, Glovsky and Popeo, P.C.

(57) ABSTRACT

Disclosed herein are methods of synthesis of a trans isomeric form of a C—C chemokine receptor type 4 (CCR4) modulator, or a salt or ester thereof that comprise making a trans isomeric compound of formula (III) by reacting a compound of formula (I) with a compound of formula (II) in the presence of a carboxylic acid directed reducing agent, wherein the compound of formula (III) is in a predominantly trans isomerically pure form.

13 Claims, No Drawings

METHODS OF MAKING TRANS ISOMERIC FORMS OF G PROTEIN-COUPLED RECEPTOR MODULATORS

CROSS-REFERENCE TO RELATED APPLICATIONS

This application claims the benefit of U.S. provisional application No. 63/144,878, filed Feb. 2, 2021, which is incorporated herein by reference in its entirety and for all purposes.

TECHNICAL FIELD

The present disclosure relates to methods of making trans isomeric forms of G protein-coupled receptor modulators of high trans isomeric purity.

BACKGROUND

Processes for making G protein-coupled receptor modulators, including C—C chemokine receptor type 4 (CCR4) inhibitors and antagonists, have been previously described. See, for example, US Patent Publication US2019/0233397 published Aug. 1, 2019 that discloses C—C chemokine receptor 4 (CCR4) inhibitors/antagonists having a trans isomeric configuration in which a carboxylic acid moiety and an amine moiety are bonded to a cycloalkyl (e.g., cyclobutane) ring in a trans isomeric configuration. In compounds such as these, when the desired modulator has a trans isomeric chemical structure, known synthetic processes tend to produce racemic mixtures of the desired and undesired isomer/diastereomer, e.g., a racemic mixture of the cis and trans isomers, making such processes non-economical for manufacturing commercial quantities of the desired trans isomer or trans diastereomer. Accordingly, it would be desirable to have a method of synthesizing trans isomeric/diastereomeric G protein-coupled receptor modulators having relatively low levels of any undesired cis isomers/diasteromer and that are economically efficient for commercial scale-up. These and other needs in the art are addressed herein.

SUMMARY

Provided herein, inter alia, are methods of synthesizing a trans isomeric form of a C—C chemokine receptor type 4 (CCR4) modulator, or a salt or ester thereof. In embodiments, the methods relate to synthesizing a trans isomeric form of a G protein-coupled receptor modulator, or a salt or ester thereof, having a 3- to 8-membered cycloalkyl ring with at least an amine moiety substitution and a carboxylic acid- or carboxylic acid-derived moiety substitution, wherein the amine moiety and carboxylic acid- or carboxylic acid derived-moiety substitutions are capable of being in a cis or a trans isomeric configuration. In embodiments, the method comprises using a 1,4-dihydropyridine as a carboxylic acid directed reducing agent of an imine or eneamine to make the modulator, or a precursor thereof, which comprises the 3- to 8-membered cycloalkyl ring having the amine moiety and carboxylic acid- or carboxylic acid derived-moiety substitutions, in a predominantly trans isomerically pure form.

In one aspect, provided herein is a method of synthesizing a trans isomeric form of a C—C chemokine receptor type 4 (CCR4) modulator, or a salt or ester thereof. In embodiments, the method comprises making a trans isomeric compound of formula (III) by reacting a compound of formula (I) with a compound of formula (II) in the presence of a carboxylic acid directed reducing agent, wherein the compound of formula (III) is in a predominantly trans isomerically pure form.

In one aspect, provided herein is a method of synthesizing a trans isomeric form of a C—C chemokine receptor type 4 (CCR4) modulator, or a salt or ester thereof. In embodiments, the method comprises making a trans isomeric compound of formula (III) by reacting a compound of formula (I) with a compound of formula (II) in the presence of a carboxylic acid directed reducing agent, wherein the compound of formula (III) is at least 80% trans isomerically pure:

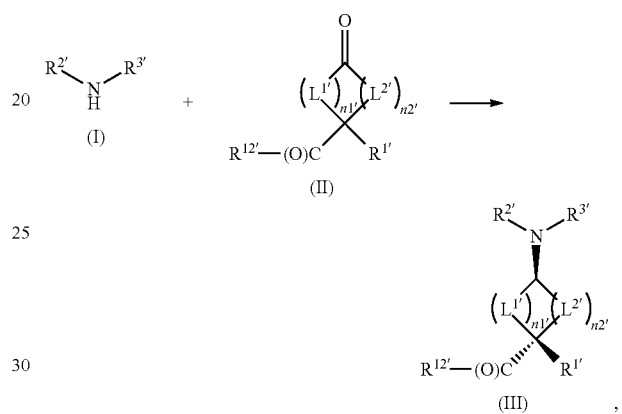

wherein:
n1' and n2' are each independently an integer from 0 to 5, wherein the sum of n1' and n2' is at least 1 and not more than 6;
$L^{1'}$ is $C(R^{4'})_2$;
$L^{2'}$ is $C(R^{5'})_2$;
$R^{1'}$ is hydrogen, halogen, $-CX^{1'}_3$, $-CHX^{1'}_2$, $-CH_2X^{1'}$, $-OCX^{1'}_3$, $-OCHX^{1'}_2$, $-OCH_2X^{1'}$, $-CN$, $-S(O)_2R^{1'A}$, $-SR^{1'A}$, $-S(O)R^{1'A}$, $-SO_2NR^{1'A}R^{1'B}$, $-NHC(O)NR^{1'A}R^{1'B}$, $-N(O)_2$, $-NR^{1'A}R^{1'B}$, $-NHNR^{1'A}R^{1'B}$, $-C(O)R^{1'A}$, $-C(O)-OR^{1'A}$, $-C(O)NR^{1'A}R^{1'B}$, $-C(O)NHNR^{1'A}R^{1'B}$, $-OR^{1'A}$, $-NR^{1'A}SO_2R^{1'B}$, $-NR^{1'A}C(O)R^{1'B}$, $-NR^{1'A}C(O)OR^{1'B}$, $-NR^{1'A}OR^{1'B}$, $-N_3$, substituted or unsubstituted alkyl, substituted or unsubstituted heteroalkyl, substituted or unsubstituted cycloalkyl, substituted or unsubstituted heterocycloalkyl; substituted or unsubstituted aryl, or substituted or unsubstituted heteroaryl;
$R^{2'}$ is hydrogen, $-CX^{2'}_3$, $-CHX^{2'}_2$, $-CH_2X^{2'}$, $-OCX^{2'}_3$, $-OCHX^{2'}_2$, $-OCH_2X^{2'}$, $-SR^{2'A}$, $\neq NR^{2'A}R^{2'B}$, $-NHNR^{2'A}R^{2'B}$, $-OR^{2'A}$, $-NR^{2'A}SO_2R^{2'B}$, $-NR^{2'A}C(O)R^{2'B}$, $-NR^{2'A}C(O)OR^{2'B}$, $-NR^{2'A}OR^{2'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl;
$R^{3'}$ is hydrogen, $-CX^{3'}_3$, $-CHX^{3'}_2$, $-CH_2X^{3'}$, $-OCX^{3'}_3$, $-OCHX^{3'}_2$, $-OCH_2X^{3'}$, $-SR^{3'A}$, $-NR^{3'A}R^{3'B}$, $-NHNR^{3'A}R^{3'B}$, $-OR^{3'A}$, $-NR^{3'A}SO_2R^{3'B}$, $-NR^{3'A}C(O)R^{3'B}$, $-NR^{3'A}C(O)OR^{3'B}$, $-NR^{3'A}OR^{3'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl;

$R^{4'}$ is hydrogen, halogen, —$CX^{4'}_3$, —$CHX^{4'}_2$, —$CH_2X^{4'}$, —$OCX^{4'}_3$, —$OCHX^{4'}_2$, —$OCH_2X^{4'}$, —CN, —$S(O)_2$ $R^{4'A}$, —$SR^{4'A}$, —$S(O)R^{4'A}$, —$SO_2NR^{4'A}R^{4'B}$, —NHC (O)NR$^{4'A}$R$^{4'B}$, —N(O)$_2$, —NR$^{4'A}$R$^{4'B}$, —NHNR$^{4'A}$R$^{4'B}$, —C(O)R$^{4'A}$, —C(O)—OR$^{4'A}$, —C(O)NR$^{4'A}$R$^{4'B}$, —C(O)NHNR$^{4'A}$R$^{4'B}$, —OR$^{4'A}$, —NR$^{4'A}$SO$_2$R$^{4'B}$, —NR$^{4'A}$C(O)R$^{4'B}$, —NR$^{4'A}$C(O) OR$^{4'B}$, —NR$^{4'A}$OR$^{4'B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5'}$ is hydrogen, halogen, —$CX^{5'}_3$, —$CHX^{5'}_2$, —$CH_2X^{5'}$, —$OCX^{5'}_3$, —$OCHX^{5'}_2$, —$OCH_2X^{5'}$, —CN, —$S(O)_2$ $R^{5'A}$, —$SR^{5'A}$, —$S(O)R^{5'A}$, —$SO_2NR^{5'A}R^{5'B}$, —NHC (O)NR$^{5'A}$R$^{5'B}$, —N(O)$_2$, —NR$^{5'A}$R$^{5'B}$, —NHNR$^{5'A}$R$^{5'B}$, —C(O)R$^{5'A}$, —C(O)—OR$^{5'A}$, —C(O)NR$^{5'A}$R$^{5'B}$, —C(O)NHNR$^{5'A}$R$^{5'B}$, —OR$^{5'A}$, —NR$^{5'A}$SO$_2$R$^{5'B}$, —NR$^{5'A}$C(O)R$^{5'B}$, —NR$^{5'A}$C(O) OR$^{5'B}$, —NR$^{5'A}$OR$^{5'B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12'}$ is independently —OH or $NHR^{12''}$;

$R^{12''}$ is hydrogen or a substituted or unsubstituted alkyl;

$R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —C(O) OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2'A}$ and $R^{2'B}$ substituents bonded to the same nitrogen atom may optionally be joined to form a substituted or unsubstituted heterocycloalkyl or substituted or unsubstituted heteroaryl; or $R^{3'A}$ and $R^{3'B}$ substituents bonded to the same nitrogen atom may optionally be joined to form a substituted or unsubstituted heterocycloalkyl or substituted or unsubstituted heteroaryl; and $X^{1'}$, $X^{2'}$, $X^{3'}$, $X^{4'}$, and $X^{5'}$ are independently halogen.

In embodiments, the compound of formula (III) is in at least 80% trans isomerically pure form. In embodiments, the compound of formula (III) is in at least 85% trans isomerically pure form. In embodiments, the compound of formula (III) is in at least 90% trans isomerically pure form. In embodiments, the compound of formula (III) is in at least 95% trans isomerically pure form. In embodiments, the compound of formula (III) is in at least 98% trans isomerically pure form. In embodiments, the compound of formula (III) is in at least 99% trans isomerically pure form. In embodiments, the compound of formula (III) is in 100% trans isomerically pure form.

In embodiments, the reacting of a compound of formula (I) with a compound of formula (II) occurs in the absence of a separate catalyst.

In embodiments, $R^{2'}$ and $R^{3'}$ are joined to form a substituted or unsubstituted piperidinyl ring. In embodiments, the piperidinyl is substituted with a substituted or unsubstituted heterocycloalkyl. In embodiments, the substituted or unsubstituted heterocycloalkyl is nitrogen-containing 3 membered to 6-membered heterocycloalkyl.

In embodiments, the compound of formula (I) is:

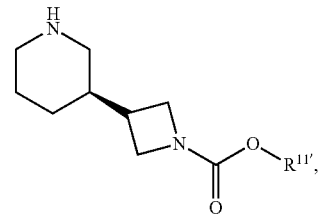

wherein:

$R^{11'''}$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{11'''}$ is a substituted or unsubstituted alkyl.

In embodiments, the compound of formula III is:

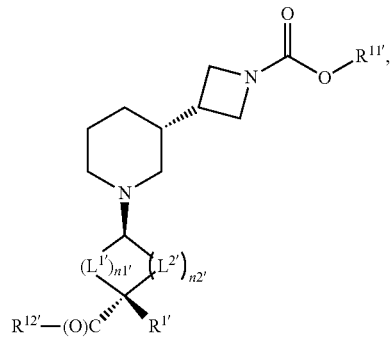

wherein $R^{11'''}$ is a substituted or unsubstituted alkyl and each of n1' and n2' is 1 or 2. $R^{1'}$, $L^{1'}$, $L^{2'}$ and $R^{12'''}$ are as described above, including embodiments.

In embodiments, the carboxylic acid directed reducing agent is a 1,4-dihydropyridine. In embodiments, the 1,4-dihydropyridine is a compound of formula (IV):

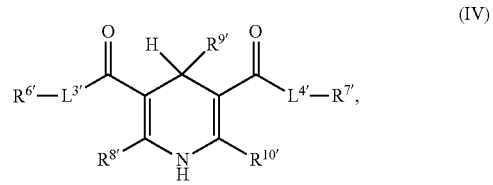

wherein:

$L^{3'}$ and $L^{4'}$ are independently O or $NR^{20'}$;

$R^{20'}$ is hydrogen or $R^{21'}$;

$R^{21'}$ is hydrogen, $-CX^{21'}_3$, $-CHX^{21'}_2$, $-CH_2X^{21'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{6'}$ is hydrogen, $-CX^{6'}_3$, $-CHX^{6'}_2$, $-CH_2X^{6'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or a bond attaching the 1,4-dihydropyridine to a polymer support;

$R^{7'}$ is hydrogen, $-CX^{7'}_3$, $-CHX^{7'}_2$, $-CH_2X^{7'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bond attaching the 1,4-dihydropyridine to a polymer support;

$R^{8'}$ is independently hydrogen, halogen, $-CX^{8'}_3$, $-CHX^{8'}_2$, $-CH_2X^{8'}$, $-OCX^{8'}_3$, $-OCHX^{8'}_2$, $-OCH_2X^{8'}$, $-CN$, $-S(O)_2R^{8'A}$, $-SR^{8'A}$, $-S(O)R^{8'A}$, $-SO_2NR^{8'A}R^{8'B}$, $-NHC(O)NR^{8'A}R^{8'B}$, $-N(O)_2$, $-NR^{8'A}R^{8'B}$, $-N^{8'A}R^{8'B}$, $-C(O)R^{8'A}$, $C(O)-R^{8'A}$, $-C(O)NR^{8'A}R^{8'B}$, $-C(O)NHNR^{8'A}R^{8'B}$, $-OR^{8'A}$, $-NR^{8'A}SO_2R^{8'B}$, $-NR^{8'A}C(O)R^{8'B}$, $-NR^{8'A}C(O)OR^{8'B}$, $-NR^{8'A}OR^{8'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{9'}$ is independently hydrogen, halogen, $-CX^{9'}_3$, $-CHX^{9'}_2$, $-CH_2X^{9'}$, $-OCX^{9'}_3$, $-OCHX^{9'}_2$, $-OCH_2X^{9'}$, $-CN$, $-S(O)_2R^{9'A}$, $-SR^{9'A}$, $-S(O)R^{9'A}$, $-SO_2NR^{9'A}R^{9'B}$, $-NHC(O)NR^{9'A}R^{9'B}$, $-N(O)_2$, $-NR^{9'A}R^{9'B}$, $-NHNR^{9'A}R^{9'B}$, $-C(O)R^{9'A}$, $-C(O)-OR^{9'A}$, $-C(O)NR^{9'A}R^{9'B}$, $-C(O)NHNR^{9'A}R^{9'B}$, $-OR^{9'A}$, $-NR^{9'A}SO_2R^{9'B}$, $-NR^{9'A}C(O)R^{9'B}$, $-NR^{9'A}C(O)OR^{9'B}$, $-NR^{9'A}OR^{9'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10'}$ is independently hydrogen, halogen, $-CX^{10'}_3$, $-CHX^{10'}_2$, $-CH_2X^{10'}$, $-OCX^{10'}_3$, $-OCHX^{10'}_2$, $-OCH_2X^{10'}$, $-CN$, $-S(O)_2R^{10'A}$, $-SR^{10'A}$, $-S(O)R^{10'A}$, $-SO_2NR^{10'A}R^{10'B}$, $-NHC(O)NR^{10'A}R^{10'B}$, $-N(O)_2$, $-NR^{10'A}R^{10'B}$, $-NHNR^{10'A}R^{10'B}$, $-C(O)R^{10'A}$, $-C(O)-OR^{10'A}$, $-C(O)NR^{10'A}R^{10'B}$, $-C(O)NHNR^{10'A}R^{10'B}$, $-OR^{10'A}$, $-NR^{10'A}SO_2R^{10'B}$, $-NR^{10'A}C(O)R^{10'B}$, $-NR^{10'A}C(O)OR^{10'B}$, $-NR^{10'A}OR^{10'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8'A}$, $R^{8'B}$, $R^{9'A}$, $R^{9'B}$, $R^{10'A}$ and $R^{10'B}$ are independently hydrogen, $-F$, $-Cl$, $-Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-C(O)OH$, $-C(O)NH_2$, $-OH$, $-NH_2$, $-COOH$, $-CONH_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^{6'}$, $X^{7'}$, $X^{8'}$, $X^{9'}$ and $X^{10'}$ are independently halogen.

These and other aspects of the present disclosure will become apparent from the following description of the preferred embodiments, although variations and modifications therein may be affected without departing from the spirit and scope of the novel concepts of the disclosure.

DETAILED DESCRIPTION

Provided herein are methods of synthesizing a trans isomeric form of a G protein-coupled receptor modulator, or a salt or ester thereof. The methods relate to synthesizing a trans isomeric form of a G protein-coupled receptor modulator, or a salt or ester thereof, having a 3- to 8-membered cycloalkyl ring with at least an amine moiety substitution and a carboxylic acid- or carboxylic acid-derived moiety substitution, wherein the amine moiety and carboxylic acid- or carboxylic acid derived-moiety substitutions are capable of being in a cis or a trans isomeric configuration.

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

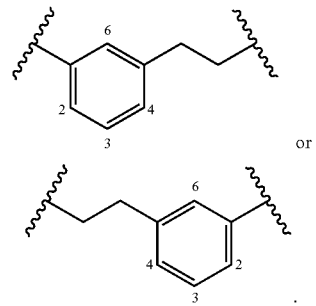

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)NHNH$_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R''')=NR"", —NR—C(NR'R")=NR'", —S(O)R', —S(O)₂R', —S(O)₂NR'R", —NRSO₂R', —NR'NR"R'", —ONR'R", —NR'C(O)NR"NR'''R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R''')=NR"", —NR—C(NR'R")=NR'", —S(O)R', —S(O)₂R', —S(O)₂NR'R", —NRSO₂R', —NR'NR"R'", —ONR'R", —NR'C(O)NR"NR'''R"", —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)₂—, or —S(O)₂NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC (O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI 2, —OCHF$_2$, unsubstituted alkyl (e.g., C$_1$-C$_8$ alkyl, C$_1$-C$_6$ alkyl, or z C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds may exist in tautomeric forms, all such tautomeric forms of the compounds being within the scope hereof.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope hereof.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope hereof.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "CCR4 inhibitor" refers to a compound (e.g., a compound described herein) capable of reducing the activity of CCR4 (e.g., by binding to CCR4) when compared to a control, such as absence of the compound or a compound with known inactivity.

The term "CCR4-mediated disease or disorder" refers to a disease or disorder that is characterized by involvement of activity and/or function of CCR4 through CCR4-mediated pathways in a body.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., USP7, p53, or Foxp3 pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein (e.g., decreased in a disease).

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition," "inhibit," "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "C—C chemokine receptor type 4" and "CCR4" refer to a protein (including homologs, isoforms, and functional fragments thereof) that is a high affinity receptor for the C—C-type chemokines (e.g., CCL2 (MCP-1), CCL4 (MIP-1), CCL5 (RANTES), CCL17 (TARC), and CCL22 (MDC)). It is referred to by a number of different names in the scientific literature, including "CC-CKR-4", "C—C CKR-4", "K5-5", "CD194", "CMKBR4", "ChemR13", "HGCN", and "14099". The term includes any recombinant or naturally-occurring form of CCR4 and/or variants thereof that maintain CCR4 activity (e.g. within at least 30%, 40%, 50%, 60%, 70%, 80%, 90%, 95%, or 100% activity compared to wildtype CCR4). The term includes any mutant form of CCR4 variants (e.g., frameshift mutations) thereof that maintain CCR4 activity (e.g. within at least 30%, 40%, 50%, 60%, 70%, 80%, 90%, 95%, or 100% activity compared to wildtype CCR4). In embodiments, the CCR4 protein encoded by the CCR4 gene has the amino acid sequence set forth in or corresponding to Entrez 1233, UniProt P51679, or RefSeq (protein) NP_005499.1. In embodiments, the CCR4 gene has the nucleic acid sequence set forth in RefSeq (mRNA) NM_005508. In embodiments, the amino acid sequence or nucleic acid sequence is the sequence known at the time of filing of the present application. In embodiments, the sequence corresponds to GI:5031627. In embodiments, the sequence corresponds to NP_005499.1. In embodiments, the sequence corresponds to NM_005508.4. In embodiments, the sequence corresponds to GI:48762930. In embodiments, the CCR4 is a human CCR4, such as a human cancer causing CCR4. Though frequently found on dendritic cells, macrophages, NK cells, platelets, and basophils, CCR4 is predominantly associated with T cells. It plays a role in the progression of multiple inflammation-related disorders, and, as described herein, has also been implicated in a number of other conditions. The genomic sequence of CCR4 is present on chromosome 3 (NC_000003.12), and the CCR4 gene is conserved in a number of species, including chimpanzee, Rhesus monkey, dog, cow, mouse, rat, chicken, and zebrafish. The CCR4 polypeptide comprises 360 amino acid residues (NP_005499.1), and, like other chemokine receptors, CCR4 is a G protein-coupled receptor that may be found on the surface of leukocytes (see, for example, Horuk (1994) Trends Pharm. Sci. 15:159-165).

The term "substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The term "trans isomerically pure form" refers to a compound having greater than about 50% of the total content of the compound, and typically greater than about 60% of the total content of the compound in a trans isomeric form. More typically, "trans isomerically pure form" refers to compounds in which at least 75%, at least 85%, at least 90%, at least 95%, at least 98%, at least 99% or more of the total compound is in a trans isomeric form (percentage in a weight per weight basis).

The terms "specifically binds" and "selectively binds," when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The term "protective group" refers to a reversibly formed derivative of an existing functional group in a molecule that is temporarily attached to decrease reactivity so that the protected functional group does not react under synthetic conditions to which the molecule is subjected in one or more subsequent steps.

The term "carboxylic acid directed reducing agent" refers to a compound that binds to a carboxylic acid moiety of a substrate compound, and reduces the substrate compound via hydride transfer. One embodiment of a carboxylic acid direct reducing agent is a 1,4-dihydropyridine, amide or mixed ester-amide, or chemical analogs thereof, all of which are referred to herein as "1,4-dihydropyridines". 1,4-dihydropyridines are a class of reducing agents that have been used in thermal catalytic hydrogenation reactions. Hantzsch esters are products of the Hantzsch dihydropyridine synthesis. They are mild reducing agents, and often used in transfer hydrogenations of activated C═C bonds, C═O bonds in carbonyl compounds, and C═N bonds in imines. An over-view of these agents is described by Wang et al., Hantzsch esters: an emerging versatile class of reagents in photoredox catalyzed organic synthesis; *Org. Biomol. Chem.*, 2019, 17, 6936-6951. In certain embodiments, a carboxylic acid directed reducing agent has one of the following two chemical formulae, the first of which is commonly called a Hantzsch ester:

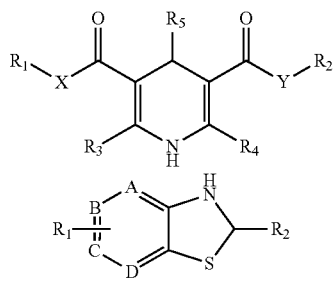

A, B, C, D = C or N in any combination except
A = B = C = D = N
A = B = C = N
B = C = D = N R1 = Me, Et, tBu, alkyl, aryl, heteroalkyl, heteroaryl, fluoroalkyl, cycloalkyl, polymer } both symmetrical and assymetrical
R2 = Me, Et, tBu, alkyl, aryl, heteroalkyl, heteroaryl, fluoroalkyl, cycloalkyl, polymer X, Y = NH, O, S, NR, where R can be alkyl, heteroalkyl, fluoroalkyl, cycloalkyl, polymer } both symmetrical and assymetrical R3 = Me, Et, tBu, alkyl, cycloalkyl, aryl, heteroalkyl, fluoroalkyl, polymer } both symmetrical and assymetrical
R4 = Me, Et, tBu, alkyl, cycloalkyl, aryl, heteroalkyl, fluoroalkyl, polymer

II. Methods of Synthesis

In one aspect, provided herein is a method of synthesizing a trans isomeric form of a C—C chemokine receptor type 4 (CCR4) modulator, or a salt or ester thereof, the method comprises making a trans isomeric compound of formula (III) by reacting a compound of formula (I) with a compound of formula (II) in the presence of a carboxylic acid directed reducing agent, wherein the compound of formula (III) is at least 80% trans isomerically pure:

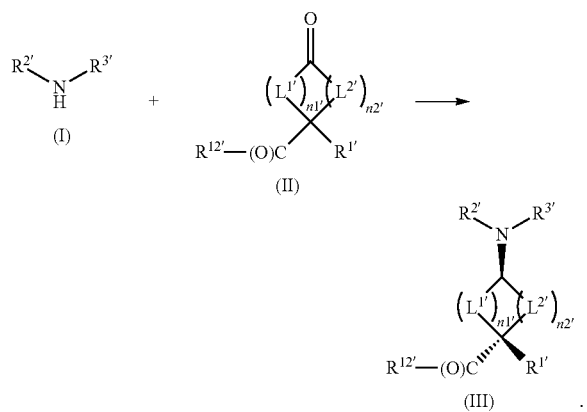

$n1'$ and $n2'$ are each independently an integer from 0 to 5, wherein the sum of $n1'$ and $n2'$ is at least 1 and not more than 6; $L^{1'}$ is $C(R^{4'})_2$; $L^{2'}$ is $C(R^{5'})_2$; $R^{1'}$ is hydrogen, halogen, —$CX^{1'}_3$, —$CHX^{1'}_2$, —$CH_2X^{1'}$, —$OCX^{1'}_3$, —$OCHX^{1'}_2$, —$OCH_2X^{1'}$, —CN, —$S(O)_2R^{1'A}$, —$SR^{1'A}$, —$S(O)R^{1'A}$, —$SO_2NR^{1'A}R^{1'B}$, —$NHC(O)NR^{1'A}R^{1'B}$, —$N(O)_2$, —$NR^{1'A}R^{1'B}$, —$NHNR^{1'A}R^{1'B}$, —$C(O)R^{1'A}$, —$C(O)OR^{1'A}$, —$C(O)NR^{1'A}R^{1'B}$, —$C(O)NHNR^{1'A}R^{1'B}$, —$OR^{1'A}$, —$NR^{1'A}SO_2R^{1'B}$, —$NR^{1'A}C(O)R^{1'B}$, —$NR^{1'A}C(O)OR^{1'B}$, —$NR^{1'A}OR^{1'B}$, —$N_3$, substituted or unsubstituted alkyl, substituted or unsubstituted heteroalkyl, substituted or unsubstituted cycloalkyl, substituted or unsubstituted heterocycloalkyl; substituted or unsubstituted aryl, or substituted or unsubstituted heteroaryl; $R^{2'}$ is hydrogen, —$CX^{2'}_3$, —$CHX^{2'}_2$, —$CH_2X^{2'}$, —$OCX^{2'}_3$, —$OCHX^{2'}_2$, —$OCH_2X^{2'}$, —$SR^{2'A}$, —$NR^{2'A}R^{2'B}$, —$NHNR^{2'A}R^{2'B}$, —$OR^{2'A}$, —$NR^{2'A}SO_2R^{2'B}$, —$NR^{2'A}C(O)R^{2'B}$, —$NR^{2'A}C(O)OR^{2'B}$, —$NR^{2'A}OR^{2'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl; $R^{3'}$ is hydrogen, —$CX^{3'}_3$, —$CHX^{3'}_2$, —$CH_2X^{3'}$, —$OCX^{3'}_3$, —$OCHX^{3'}_2$, —$OCH_2X^{3'}$, —$SR^{3'A}$, —$NR^{3'A}R^{3'B}$, —$NHNR^{3'A}R^{3'B}$, —$OR^{3'A}$, —$NR^{3'A}SO_2R^{3'B}$, —$NR^{3'A}C(O)R^{3'B}$, —$NR^{3'A}C(O)OR^{3'B}$, —$NR^{3'A}OR^{3'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl; $R^{4'}$ is hydrogen, halogen, —$CX^{4'}_3$, —$CHX^{4'}_2$, —$CH_2X^{4'}$, —$OCX^{4'}_3$, —$OCHX^{4'}_2$, —$OCH_2X^{4'}$, —CN, —$S(O)_2R^{4'A}$, —$SR^{4'A}$, —$S(O)R^{4'A}$, —$SO_2NR^{4'A}R^{4'B}$, —$NHC(O)NR^{4'A}R^{4'B}$, —$N(O)_2$, —$NR^{4'A}R^{4'B}$, —$NHNR^{4'A}R^{4'B}$, —$C(O)R^{4'A}$, —$C(O)OR^{4'A}$, —$C(O)NR^{4'A}R^{4'B}$, —$C(O)NHNR^{4'A}R^{4'B}$, —$OR^{4'A}$, —$NR^{4'A}SO_2R^{4'B}$, —$NR^{4'A}C(O)R^{4'B}$, —$NR^{4'A}C(O)OR^{4'B}$, —$NR^{4'A}OR^{4'B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5'}$ is independently hydrogen, halogen, —$CX^{5'}_3$, —$CHX^{5'}_2$, —$CH_2X^{5'}$, —$OCX^{5'}_3$, —$OCHX^{5'}_2$, —$OCH_2X^{5'}$, —CN, —$S(O)_2R^{5'A}$, —$SR^{5'A}$, —$S(O)R^{5'A}$, —$SO_2NR^{5'A}R^{5'B}$, —$NHC(O)NR^{5'A}R^{5'B}$, —$N(O)_2$, —$NR^{5'A}R^{5'B}$, —$NHNR^{5'A}R^{5'B}$, —$C(O)R^{5'A}$, —$C(O)OR^{5'A}$, —$C(O)NR^{5'A}R^{5'B}$, —$C(O)NHNR^{5'A}R^{5'B}$, —$OR^{5'A}$, —$NR^{5'A}SO_2R^{5'B}$, —$NR^{5'A}C(O)R^{5'B}$, —$NR^{5'A}C(O)OR^{5'B}$, —$NR^{5'A}OR^{5'B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12'}$ is independently —OH or $NHR^{12''}$; $R^{12''}$ is hydrogen or a substituted or unsubstituted alkyl; $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —C(O)OH, —C(O)$NH_2$, —OH, —$NH_2$, —COOH, —$CONH_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2'A}$ and $R^{2'B}$ substituents bonded to the same nitrogen atom may optionally be joined to form a substituted or unsubstituted heterocycloalkyl or substituted or unsubstituted heteroaryl; or $R^{3'A}$ and $R^{3'B}$ substituents bonded to the same nitrogen atom may optionally be joined to form a substituted or unsubstituted heterocycloalkyl or substituted or unsubstituted heteroaryl; and $X^{1'}$, $X^{2'}$, $X^{3'}$, $X^{4'}$, and $X^{5'}$ are independently halogen.

In embodiments, the compound of formula (III) is in at least 85% trans isomerically pure form. In embodiments, the compound of formula (III) is in at least 90% trans isomerically pure form. In embodiments, the compound of formula (III) is in at least 95% trans isomerically pure form. In embodiments, the compound of formula (III) is in at least 98% trans isomerically pure form. In embodiments, the compound of formula (III) is in at least 99% trans isomerically pure form. In embodiments, the compound of formula (III) is in 100% trans isomerically pure form.

In embodiments, n1' and n2' are each independently an integer from 0 to 5, wherein the sum of n1' and n2' is at least 1 and not more than 6.

In embodiments, $L^{1'}$ is $C(R^{4'})_2$.

$R^{4'}$ is independently hydrogen, halogen, —$CX^{4'}_3$, —$CHX^{4'}_2$, —$CH_2X^{4'}$, —$OCX^{4'}_3$, —$OCHX^{4'}_2$, —$OCH_2X^{4'}$, —CN, —$S(O)_2R^{4'A}$, —$SR^{4'A}$, —$S(O)R^{4'A}$, —$SO_2NR^{4'A}R^{4'B}$, —$NHC(O)NR^{4'A}R^{4'B}$, —$N(O)_2$, —$NR^{4'A}R^{4'B}$, —$NHNR^{4'A}R^{4'B}$, —$C(O)R^{4'A}$, —$C(O)$—$OR^{4'A}$, —$C(O)NR^{4'A}R^{4'B}$, —$C(O)NHNR^{4'A}R^{4'B}$, —$OR^{4'A}$, —$NR^{4'A}SO_2R^{4'B}$, —$NR^{4'A}C(O)R^{4'B}$, —$NR^{4'A}C(O)OR^{4'B}$, —$NR^{4'A}OR^{4'B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

In embodiments, $R^{4'}$ is hydrogen, halogen (e.g., —F, —Cl, Br, —I), —$CX^{4'}_3$, —$CX^{4'}_2$, —$CH_2X^{4'}$, —$OCX^{4'}_3$, —$OCHX^{4'}_2$, —$OCH_2X^{4'}$, —CN, —$S(O)_2R^{4'A}$, —$SR^{4'A}$, —$S(O)R^{4'A}$, —$SO_2NR^{4'A}R^{4'B}$, —$NHC(O)NR^{4'A}R^{4'B}$, —$N(O)_2$, —$NR^{4'A}R^{4'B}$, —$NHNR^{4'A}R^{4'B}$, —$C(O)R^{4'A}$, —$C(O)$—$OR^{4'A}$, —$C(O)NR^{4'A}R^{4'B}$, —$C(O)NHNR^{4'A}R^{4'B}$, —$OR^{4'A}$, —$NR^{4'A}SO_2R^{4'B}$, —$NR^{4'A}C(O)R^{4'B}$, —$NR^{4'A}C(O)OR^{4'B}$, —$NR^{4'A}OR^{4'B}$, —$N_3$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^{4'}$ is independently —F, —Cl, —Br, or —I.

In embodiments, $R^{4'}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{4'}$ is substituted, $R^{4'}$ is substituted with a substituent group. In embodiments, where $R^{4'}$ is substituted, $R^{4'}$ is substituted with a size-limited substituent group. In embodiments, where $R^{4'}$ is substituted, $R^{4'}$ is substituted with a lower substituent group.

In embodiments, $R^{4'}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $L^{2'}$ is $C(R^{5'})_2$.

$R^{5'}$ is independently hydrogen, halogen, —$CX^{5'}_3$, —$CHX^{5'}_2$, —$CH_2X^{5'}$, —$OCX^{5'}_3$, —$OCHX^{5'}_2$, —$OCH_2X^{5'}$, —CN, —$S(O)_2R^{5'A}$, —$SR^{5'A}$, —$S(O)R^{5'A}$, —$SO_2NR^{5'A}R^{5'B}$, —$NHC(O)NR^{5'A}R^{5'B}$, —$N(O)_2$, —$NR^{5'A}R^{5'B}$, —$NHNR^{5'A}R^{5'B}$, —$C(O)R^{5'A}$, —$C(O)$—$OR^{5'A}$, —$C(O)NR^{5'A}R^{5'B}$, —$C(O)NHNR^{5'A}R^{5'B}$, —$OR^{5'A}$, —NR$^{5'A}$SO$_2$R$^{5'B}$, —NR$^{5'A}$C(O)R$^{5'B}$, —NR$^{5'A}$C(O)OR$^{5'B}$, —NR$^{5'A}$OR$^{5'B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl In embodiments, R$^{5'}$ is hydrogen, halogen (e.g., —F, —Cl, Br, —I), —CX$^{5'}_3$, —CHX$^{5'}_2$, —CH$_2$X$^{5'}$, —OCX$^{5'}_3$, —OCHX$^{5'}_2$, —OCH$_2$X$^{5'}$, —CN, —S(O)$_2$R$^{5'A}$, —SR$^{5'A}$, —S(O)R$^{5'A}$, —SO$_2$NR$^{5'A}$R$^{5'B}$, —NHC(O)NR$^{5'A}$R$^{5'B}$, —N(O)$_2$, —NR$^{5'A}$R$^{5'B}$, —NHNR$^{5'A}$R$^{5'B}$, —C(O)R$^{5'A}$, —C(O)— OR$^{5'A}$, —C(O)NR$^{5'A}$R$^{5'B}$, —C(O)NHNR$^{5'A}$R$^{5'B}$, —OR$^{5'A}$, —NR$^{5'A}$SO$_2$R$^{5'B}$, —NR$^{5'A}$C(O)R$^{5'B}$, —NR$^{5'A}$C(O)OR$^{5'B}$, —NR$^{5'A}$OR$^{5'B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^{5'}$ is independently —F, —Cl, —Br, or —I.

In embodiments, R$^{5'}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, 13 OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where R$^{5'}$ is substituted, R$^{5'}$ is substituted with a substituent group. In embodiments, where R$^{5'}$ is substituted, R$^{5'}$ is substituted with a size-limited substituent group. In embodiments, where R$^{5'}$ is substituted, R$^{5'}$ is substituted with a lower substituent group.

In embodiments, R$^{5'}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

R$^{1'}$ is hydrogen, halogen, —CX$^{1'}_3$, —CHX$^{1'}_2$, —CH$_2$X$^{1'}$, —OCX$^{1'}_3$, —OCHX$^{1'}_2$, —OCH$_2$X$^{1'}$, —CN, —S(O)$_2$R$^{1'A}$, —SR$^{1'A}$, —S(O)R$^{1'A}$, —SO$_2$NR$^{1'A}$R$^{1'B}$, —NHC(O)NR$^{1'A}$R$^{1'B}$, —N(O)$_2$, —NR$^{1'A}$R$^{1'B}$, —NHNR$^{1'A}$R$^{1'B}$, —C(O)R$^{1'A}$, —C(O)—OR$^{1'A}$, —C(O)NR$^{1'A}$R$^{1'B}$, —C(O)NHNR$^{1'A}$R$^{1'B}$, —OR$^{1'A}$, —NR$^{1'A}$SO$_2$R$^{1'B}$, —NR$^{1'A}$C(O)R$^{1'B}$, —NR$^{1'A}$C(O)OR$^{1'B}$, —NR$^{1'A}$OR$^{1'B}$, —N$_3$, substituted or unsubstituted alkyl, substituted or unsubstituted heteroalkyl, substituted or unsubstituted cycloalkyl, substituted or unsubstituted heterocycloalkyl; substituted or unsubstituted aryl, or substituted or unsubstituted heteroaryl.

In embodiments, R$^{1'}$ is hydrogen, halogen (e.g., —F, —Cl, Br, —I), —CX$^{1'}_3$, —CHX$^{1'}_2$, —CH$_2$X$^{1'}$, —OCX$^{1'}_3$, —OCHX$^{1'}_2$, —OCH$_2$X$^{1'}$, —CN, —S(O)$_2$R$^{1'A}$, —SR$^{1'A}$, —S(O)R$^{1'A}$, —SO$_2$NR$^{1'A}$R$^{1'B}$, —NHC(O)NR$^{1'A}$R$^{1'B}$, —N(O)$_2$, —NR$^{1'A}$R$^{1'B}$, —NHNR$^{1'A}$R$^{1'B}$, —C(O)R$^{1'A}$, —C(O)—OR$^{1'A}$, —C(O)NR$^{1'A}$R$^{1'B}$, —C(O)NHNR$^{1'A}$R$^{1'B}$, —OR$^{1'A}$, —NR$^{1'A}$SO$_2$R$^{1'B}$, —NR$^{1'A}$C(O)R$^{1'B}$, —NR$^{1'A}$C(O)OR$^{1'B}$, —NR$^{1'A}$OR$^{1'B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^{1'}$ is independently —F, —Cl, —Br, or —I.

In embodiments, $R^{1'}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{1'}$ is substituted, $R^{1'}$ is substituted with a substituent group. In embodiments, where $R^{1'}$ is substituted, $R^{1'}$ is substituted with a size-limited substituent group. In embodiments, where $R^{1'}$ is substituted, $R^{1'}$ is substituted with a lower substituent group.

In embodiments, $R^{1'}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

$R^{2'}$ is hydrogen, —$CX^{2'}_3$, —$CHX^{2'}_2$, —$CH_2X^{2'}$, —$OCX^{2'}_3$, —$OCHX^{2'}_2$, —$OCH_2X^{2'}$, —$SR^{2'A}$, —$NR^{2'A}R^{2'B}$, —$NHNR^{2'A}R^{2'B}$, —$OR^{2'A}$, —$NR^{2'A}SO_2R^{2'B}$, —$NR^{2'A}C(O)R^{2'B}$, —$NR^{2'A}C(O)OR^{2'B}$, —$NR^{2'A}OR^{2'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl. In embodiments, where $R^{2'}$ and $R^{3'}$ are joined to form a substituted heterocycloalkyl, the heterocycloalkyl is substituted with a substituent group. In embodiments, where $R^{2'}$ and $R^{3'}$ are joined to form a substituted heterocycloalkyl, the heterocycloalkyl is substituted with a size-limited substituent group. In embodiments, where $R^{2'}$ and $R^{3'}$ are joined to form a substituted heterocycloalkyl, the heterocycloalkyl is substituted with a lower substituent group.

In embodiments, $R^{2'}$ is hydrogen, —$CX^{2'}_3$, —$CHX^{2'}_2$, —$CH_2X^{2'}$, —$OCX^{2'}_3$, —$OCHX^{2'}_2$, —$OCH_2X^{2'}$, —$SR^{2'A}$, —$NR^{2'A}R^{2'B}$, —$NHNR^{2'A}R^{2'B}$, —$OR^{2'A}$, —$NR^{2'A}SO_2R^{2'B}$, —$NR^{2'A}C(O)R^{2'B}$, —$NR^{2'A}C(O)OR^{2'B}$, —$NR^{2'A}OR^{2'B}$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^{2'}$ is independently —F, —Cl, —Br, or —I.

In embodiments, $R^{2'}$ is hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where R$^{2'}$ is substituted, R$^{2'}$ is substituted with a substituent group. In embodiments, where R$^{2'}$ is substituted, R$^{2'}$ is substituted with a size-limited substituent group. In embodiments, where R$^{2'}$ is substituted, R$^{2'}$ is substituted with a lower substituent group.

In embodiments, R$^{2'}$ is hydrogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

R$^{3'}$ is hydrogen, —CX$^{3'}_3$, —CHX$^{3'}_2$, —CH$_2$X$^{3'}$, —OCX$^{3'}_3$, —OCHX$^{3'}_2$, —OCH$_2$X$^{3'}$, —SR$^{3'A}$, —NR$^{3'A}$R$^{3'B}$, —NHNR$^{3'A}$R$^{3'B}$, —OR$^{3'A}$, —NR$^{3'A}$SO$_2$R$^{3'B}$, —NR$^{3'A}$C(O)R$^{3'B}$, —NR$^{3'A}$C(O)OR$^{3'B}$, —NR$^{3'A}$OR$^{3'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein R$^{2'}$ and R$^{3'}$ may optionally be joined to form a substituted or unsubstituted heterocycloalkyl.

In embodiments, R$^{3'}$ is hydrogen, —CX$^{3'}_3$, —CHX$^{3'}_2$, —CH$_2$X$^{3'}$, —OCX$^{3'}_3$, —OCHX$^{3'}_2$, —OCH$_2$X$^{3'}$, —SR$^{3'A}$, —NR$^{3'A}$R$^{3'B}$, —NHNR$^{3'A}$R$^{3'B}$, —OR$^{3'A}$, —NR$^{3'A}$SO$_2$R$^{3'B}$, —NR$^{3'A}$C(O)R$^{3'B}$, —NR$^{3'A}$C(O)OR$^{3'B}$, —NR$^{3'A}$OR$^{3'B}$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^{3'}$ is independently —F, —Cl, —Br, or —I.

In embodiments, R$^{3'}$ is hydrogen, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where R$^{3'}$ is substituted, R$^{3'}$ is substituted with a substituent group. In embodiments, where R$^{3'}$ is substituted, R$^{3'}$ is substituted with a size-limited substituent group. In embodiments, where $R^{3'}$ is substituted, $R^{3'}$ is substituted with a lower substituent group.

In embodiments, $R^{3'}$ is hydrogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)H, —NHOH, —NCH$_3$OH, or —NCH$_3$OCH$_3$), unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{2'}$ and $R^{3'}$ are joined to form a substituted or unsubstituted piperidinyl ring. In embodiments, the piperidinyl is substituted with a substituted or unsubstituted heterocycloalkyl. In embodiments, the substituted or unsubstituted heterocycloalkyl is nitrogen-containing 3-membered to 6-membered heterocycloalkyl.

$R^{12'}$ is independently —OH or NHR$^{12''}$. In embodiments, $R^{12'}$ is —OH. In embodiments, $R^{12'}$ is NHR$^{12''}$.

$R^{12''}$ is hydrogen or a substituted or unsubstituted alkyl. In embodiments, $R^{12''}$ is hydrogen. In embodiments, $R^{12''}$ is a substituted or unsubstituted alkyl. In embodiments, $R^{12''}$ is substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{12''}$ is substituted with a substituent group. In embodiments, $R^{12''}$ is substituted with a size-limited substituent group. In embodiments, $R^{12''}$ is substituted with a lower substituent group.

$R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2'A}$ and $R^{2'B}$ substituents bonded to the same nitrogen atom may optionally be joined to form a substituted or unsubstituted heterocycloalkyl or substituted or unsubstituted heteroaryl; or $R^{3'A}$ and $R^{3'B}$ substituents bonded to the same nitrogen atom may optionally be joined to form a substituted or unsubstituted heterocycloalkyl or substituted or unsubstituted heteroaryl.

In embodiments, $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted, $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted with a substituent group. In embodiments, where $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted, $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted with a size-limited substituent group. In embodiments, where $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted, $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ is substituted with a lower substituent group. In embodiments, $R^{1'A}$ is substituted with a substituent group. In embodiments, $R^{1'A}$ is substituted with a size-limited substituent group. In embodiments, $R^{1'A}$ is substituted with a lower substituent group. In embodiments, $R^{1'B}$ is substituted with a substituent group. In embodiments, $R^{1'B}$ is substituted with a size-limited substituent group. In embodiments, $R^{1'B}$ is substituted with a lower substituent group. In embodiments, $R^{2'A}$ is substituted with a substituent group. In embodiments, $R^{2'A}$ is substituted with a size-limited substituent group. In embodiments, $R^{2'A}$ is substituted with a lower substituent group. In embodiments, $R^{2'B}$ is substituted with a substituent group. In embodiments, $R^{2'B}$ is substituted with a size-limited substituent group. In embodiments, $R^{2'B}$ is substituted with a lower substituent group. In embodiments, $R^{3'A}$ is substituted with a substituent group. In embodiments, $R^{3'A}$ is substituted with a size-limited substituent group. In embodiments, $R^{3'A}$ is substituted with a lower substituent group. In embodiments, $R^{3'B}$ is substituted with a substituent group. In embodiments, $R^{3'B}$ is substituted with a size-limited substituent group. In embodiments, $R^{3'B}$ is substituted with a lower substituent group. In embodiments, $R^{4'A}$ is substituted with a substituent group. In embodiments, $R^{4'A}$ is substituted with a size-limited substituent group. In embodiments, $R^{4'A}$ is substituted with a lower substituent group. In embodiments, $R^{4'B}$ is substituted with a substituent group. In embodiments, $R^{4'B}$ is substituted with a size-limited substituent group. In embodiments, $R^{4'B}$ is substituted with a lower substituent group. In embodiments, $R^{5'A}$ is substituted with a substituent group. In embodiments, $R^{5'A}$ is substituted with a size-limited substituent group. In embodiments, $R^{5'A}$ is substituted with a lower substituent group. In embodiments, $R^{5'B}$ is substituted with a substituent group. In embodiments, $R^{5'B}$ is substituted with a size-limited substituent group. In embodiments, $R^{5'B}$ is substituted with a lower substituent group.

In embodiments, $R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, —F, —Cl, —Br, —I, —CF$_3$, —CHF$_2$, —CHF$_2$, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, the reacting of a compound of formula (I) with a compound of formula (II) occurs in the absence of a separate catalyst.

In embodiments, the compound of formula (I) is:

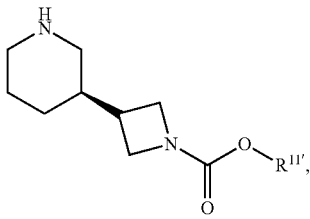

wherein $R^{1'}$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1'}$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NH$_2$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{11'''}$ is substituted, $R^{11'''}$ is substituted with a substituent group. In embodiments, where $R^{11'''}$ is substituted, $R^{11'''}$ is substituted with a size-limited substituent group. In embodiments, where $R^{11'''}$ is substituted, $R^{11'''}$ is substituted with a lower substituent group.

In embodiments, $R^{11'''}$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NH$_2$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, $R^{11'''}$ is a substituted or unsubstituted alkyl. In embodiments, $R^{11'''}$ is a substituted (e.g., substituted with a substituent group, a size-limited substituent group, or lower substituent group) or unsubstituted alkyl (e.g., C$_1$-C$_8$, C$_1$-C$_6$, or C$_1$-C$_4$).

In embodiments, the compound of formula III is:

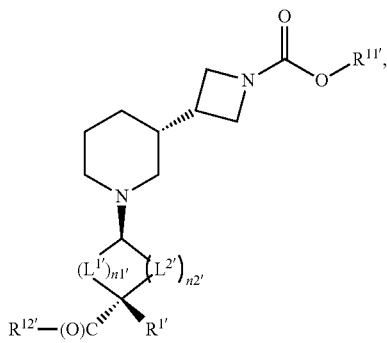

wherein $R^{11'}$ is a substituted or unsubstituted alkyl and each of n1' and n2' is 1 or 2. $R^{1'}$, $L^{1'}$, $L^{2'}$, and $R^{12'}$ are as described above, including embodiments.

In embodiments, the compound of formula III is:

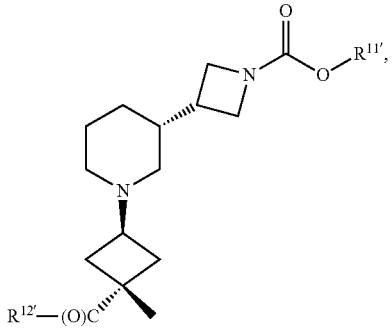

wherein $R^{12'}$ is a substituted or unsubstituted alkyl.

In the synthetic methods provided herein, the carboxylic acid directed reducing agent is a 1,4-dihydropyridine of formula (IV):

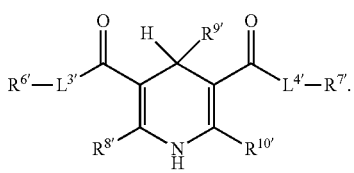

(IV)

$L^{3'}$ and $L^{4'}$ are independently O or $NR^{20'}$; $R^{20'}$ is hydrogen or $R^{21'}$; $R^{21'}$ is hydrogen, $-CX^{21'}_3$, $-CHX^{21'}_2$, $-CH_2X^{21'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{6'}$ is hydrogen, $-CX^{6'}_3$, $-CHX^{6'}_2$, $-CH_2X^{6'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or a bond attaching the 1,4-dihydropyridine to a polymer support; $R^{7'}$ is hydrogen, $-CX^{7'}_3$, $-CHX^{7'}_2$, $-CH_2X^{7'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bond attaching the 1,4-dihydropyridine to a polymer support; $R^{8'}$ is independently hydrogen, halogen, $-CX^{8'}_3$, $-CHX^{8'}_2$, $-CH_2X^{8'}$, $-OCX^{8'}_3$, $-OCHX^{8'}_2$, $-OCH_2X^{8'}$, $-CN$, $-S(O)_2R^{8'A}$, $-SR^{8'A}$, $-S(O)R^{8'A}$, $-SO_2NR^{8'A}R^{8'B}$, $-NHC(O)NR^{8'A}R^{8'B}$, $-N(O)_2$, $-NR^{8'A}R^{8'B}$, $-NHNR^{8'A}R^{8'B}$, $-C(O)R^{8'A}$, $-C(O)-OR^{8'A}$, $-C(O)NR^{8'A}R^{8'B}$, $-C(O)NHNR^{8'A}R^{8'B}$, $-OR^{8'A}$, $-NR^{8'A}SO_2R^{8'B}$, $-NR^{8'A}C(O)R^{8'B}$, $-NR^{8'A}C(O)OR^{8'B}$, $-NR^{8'A}OR^{8'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{9'}$ is independently hydrogen, halogen, $-CX^{9'}_3$, $-CHX^{9'}_2$, $-CH_2X^{9'}$, $-OCX^{9'}_3$, $-OCHX^{9'}_2$, $-OCH_2X^{9'}$, $-CN$, $-S(O)_2R^{9'A}$, $-SR^{9'A}$, $-S(O)R^{9'A}$, $-SO_2NR^{9'A}R^{9'B}$, $-NHC(O)NR^{9'A}R^{9'B}$, $-N(O)_2$, $-NR^{9'A}R^{9'B}$, $-NHNR^{9'A}R^{9'B}$, $-C(O)R^{9'A}$, $-C(O)-OR^{9'A}$, $-C(O)NR^{9'A}R^{9'B}$, $-C(O)NHNR^{9'A}R^{9'B}$, $-OR^{9'A}$, $-NR^{9'A}SO_2R^{9'B}$, $-NR^{9'A}C(O)R^{9'B}$, $-NR^{9'A}C(O)OR^{9'B}$, $-NR^{9'A}OR^{9'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10'}$ is independently hydrogen, halogen, $-CX^{10'}_3$, $-CHX^{10'}_2$, $-CH_2X^{10'}$, $-OCX^{10'}_3$, $-OCHX^{10'}_2$, $-OCH_2X^{10'}$, $-CN$, $-S(O)_2R^{10'A}$, $-SR^{10'A}$, $-S(O)R^{10'A}$, $-SO_2NR^{10'A}R^{10'B}$, $-NHC(O)NR^{10'A}R^{10'B}$, $-N(O)_2$, $-NR^{10'A}R^{10'B}$, $-NHNR^{10'A}R^{10'B}$, $-C(O)R^{10'A}$, $-C(O)-OR^{10'A}$, $-C(O)NR^{10'A}R^{10'B}$, $-C(O)NHNR^{10'A}R^{10'B}$, $-OR^{10'A}$, $-NR^{10'A}SO_2R^{10'B}$, $-NR^{10'A}C(O)R^{10'B}$, $-NR^{10'A}C(O)OR^{10'B}$, $-NR^{10'A}OR^{10'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{8'A}$, $R^{8'B}$, $R^{9'A}$, $R^{9'B}$, $R^{10'A}$ and $R^{10'B}$ are independently hydrogen, $-F$, $-Cl$, $-Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-C(O)OH$, $-C(O)NH_2$, $-OH$, $-NH_2$, $-COOH$, $-CONH_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^{6'}$, $X^{7'}$, $X^{8'}$, $X^{9'}$ and $X^{10'}$ are independently halogen.

In embodiments, $L^{3'}$ is O or $NR^{20'}$. In embodiments, $L^{3'}$ is O. In embodiments, $L^{3'}$ is $NR^{20'}$. In embodiments, $L^{3'}$ is O or $NR^{21'}$.

In embodiments, $L^{4'}$ is O or $NR^{20'}$. In embodiments, $L^{4'}$ is O. In embodiments, $L^{4'}$ is $NR^{20'}$. In embodiments, $L^{4'}$ is O or $NR^{21'}$.

In embodiments, $R^{20'}$ is hydrogen or $R^{21'}$. In embodiments, $R^{20'}$ is hydrogen. In embodiments, $R^{20'}$ is $R^{21'}$.

In embodiments, $R^{21'}$ is hydrogen, $-CX^{21'}_3$, $-CHX^{21'}_2$, $-CH_2X^{21'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In embodiments, $R^{21'}$ is hydrogen, $-CX^{21'}_3$, $-CHX^{21'}_2$, $-CH_2X^{21'}$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{21'}$ is substituted, $R^{21'}$ is substituted with a substituent group. In embodiments, where $R^{21'}$ is substituted, $R^{21'}$ is substituted with a size-limited substituent group. In embodiments, where $R^{21'}$ is substituted, $R^{21'}$ is substituted with a lower substituent group.

In embodiments, $R^{21'}$ is hydrogen, $-CX^{21'}_3$, $-CHX^{21'}_2$, $-CH_2X^{21'}$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{6'}$ is hydrogen, $-CX^{6'}_3$, $-CHX^{6'}_2$, $-CH_2X^{6'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or a bond attaching the 1,4-dihydropyridine to a polymer support. $X^{6'}$ is independently —F, —Cl, —Br, or —I.

In embodiments, $R^{6'}$ is hydrogen, —$CX^{6'}_3$, —$CHX^{6'}_2$, —$CH_2X^{6'}$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered), or a bond attaching the 1,4-dihydropyridine to a polymer support. $X^{6'}$ is independently —F, —Cl, —Br, or —I.

In embodiments, $R^{6'}$ is hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered), or a bond attaching the 1,4-dihydropyridine to a polymer support. In embodiments, where $R^{6'}$ is substituted, $R^{6'}$ is substituted with a substituent group. In embodiments, where $R^{6'}$ is substituted, $R^{6'}$ is substituted with a size-limited substituent group. In embodiments, where $R^{6'}$ is substituted, $R^{6'}$ is substituted with a lower substituent group.

In embodiments, $R^{6'}$ is hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered), or a bond attaching the 1,4-dihydropyridine to a polymer support.

In embodiments, $R^{7'}$ is hydrogen, —$CX^{7'}_3$, —$CHX^{7'}_2$, —$CH_2X^{7'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bond attaching the 1,4-dihydropyridine to a polymer support. $X^{7'}$ is independently —F, —Cl, —Br, or —I.

In embodiments, $R^{7'}$ is independently hydrogen, —$CX^{7'}_3$, —$CHX^{7'}_2$, —$CH_2X^{7'}$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered), or a bond attaching the 1,4-dihydropyridine to a polymer support. $X^{7'}$ is independently —F, —Cl, —Br, or —I.

In embodiments, $R^{7'}$ is independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered), or a bond attaching the 1,4-dihydropyridine to a polymer support. In embodiments, where $R^{7'}$ is substituted, $R^{7'}$ is substituted with a substituent group. In embodiments, where $R^{7'}$ is substituted, $R^{7'}$ is substituted with a size-limited substituent group. In embodiments, where $R^{7'}$ is substituted, $R^{7'}$ is substituted with a lower substituent group.

In embodiments, $R^{7'}$ is independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered), or a bond attaching the 1,4-dihydropyridine to a polymer support.

$R^{8'}$ is independently hydrogen, halogen, —$CX^{8'}_3$, —$CHX^{8'}_2$, —$CH_2X^{8'}$, —$OCX^{8'}_3$, —$OCHX^{8'}_2$, —$OCH_2X^{8'}$, —CN, —$S(O)_2R^{8'A}$, —$SR^{8'A}$, —$S(O)R^{8'A}$, —$SO_2NR^{8'A}R^{8'B}$, —$NHC(O)NR^{8'A}R^{8'B}$, —$N(O)_2$, —$NR^{8'A}R^{8'B}$, —$NHNR^{8'A}R^{8'B}$, —$C(O)R^{8'A}$, —$C(O)$—$OR^{8'A}$, —$C(O)NR^{8'A}R^{8'B}$, —$C(O)NHNR^{8'A}R^{8'B}$, —$OR^{8'A}$, —$NR^{8'A}SO_2R^{8'B}$, —$NR^{8'A}C(O)R^{8'B}$, —$NR^{8'A}C(O)OR^{8'B}$, —$NR^{8'A}OR^{8'B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{8'}$ is independently —F, —Cl, —Br, or —I.

In embodiments, $R^{8'}$ is independently hydrogen, halogen, (e.g., —F, —Cl, Br, —I), —$CX^{8'}_3$, —$CHX^{8'}_2$, —$CH_2X^{8'}$, —$OCX^{8'}_3$, —$OCHX^{8'}_2$, —$OCH_2X^{8'}$, —CN, —$S(O)_2R^{8'A}$, —$SR^{8'A}$, —$S(O)R^{8'A}$, —$SO_2NR^{8'A}R^{8'B}$, —$NHC(O)NR^{8'A}R^{8'B}$, —$N(O)_2$, —$NR^{8'A}R^{8'B}$, —$NHNR^{8'A}R^{8'B}$, —$C(O)R^{8'A}$, —$C(O)$—$OR^{8'A}$, —$C(O)NR^{8'A}R^{8'B}$, —$C(O)NHNR^{8'A}R^{8'B}$, —$OR^{8'A}$, —$NR^{8'A}SO_2R^{8'B}$, —$NR^{8'A}C(O)R^{8'B}$, —$NR^{8'A}C(O)OR^{8'B}$, —$NR^{8'A}OR^{8'B}$, —$N_3$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^{8'}$ is independently —F, —Cl, —Br, or —I.

In embodiments, $R^{8'}$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{8'}$ is substituted, $R^{8'}$ is substituted with a substituent group. In embodiments, where $R^{8'}$ is substituted, $R^{8'}$ is substituted with a size-limited substituent group. In embodiments, where $R^{8'}$ is substituted, $R^{8'}$ is substituted with a lower substituent group.

In embodiments, $R^{8'}$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

$R^{9'}$ is independently hydrogen, halogen, —$CX^{9'}_3$, —$CHX^{9'}_2$, —$CH_2X^{9'}$, —$OCX^{9'}_3$, —$OCHX^{9'}_2$, —$OCH_2X^{9'}$, —CN, —$S(O)_2R^{9'A}$, —$SR^{9'A}$, —$S(O)R^{9'A}$, —$SO_2NR^{9'A}R^{9'B}$, —$NHC(O)NR^{9'A}R^{9'B}$, —$N(O)_2$, —$NR^{9'A}R^{9'B}$, —$NHNR^{9'A}R^{9'B}$, —$C(O)R^{9'A}$, —$C(O)$—$OR^{9'A}$, —$C(O)NR^{9'A}R^{9'B}$, —$C(O)NHNR^{9'A}R^{9'B}$, —$OR^{9'A}$, —$NR^{9'A}SO_2R^{9'B}$, —$NR^{9'A}C(O)R^{9'B}$, —$NR^{9'A}C(O)OR^{9'B}$, —$NR^{9'A}OR^{9'B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{9'}$ is independently —F, —Cl, —Br, or —I.

In embodiments, $R^{9'}$ is independently hydrogen, halogen, (e.g., —F, —Cl, Br, —I), —$CX^{9'}_3$, —$CHX^{9'}_2$, —$CH_2X^{9'}$, —$OCX^{9'}_3$, —$OCHX^{9'}_2$, —$OCH_2X^{9'}$, —CN, —$S(O)_2R^{9'A}$, —$SR^{9'A}$, —$S(O)R^{9'A}$, —$SO_2NR^{9'A}R^{9'B}$, —$NHC(O)NR^{9'A}R^{9'B}$, —$N(O)_2$, —$NR^{9'A}R^{9'B}$, —$NHNR^{9'A}R^{9'B}$, —$C(O)R^{9'A}$, —$C(O)$—$OR^{9'A}$, —$C(O)NR^{9'A}R^{9'B}$, —$C(O)$ NHNR$^{9'A}$R$^{9'B}$, —OR$^{9'A}$, —NR$^{9'A}$SO$_2$R$^{9'B}$, —NR$^{9'A}$C(O)R$^{9'B}$, —NR$^{9'A}$C(O)OR$^{9'B}$, —NR$^{9'A}$OR$^{9'B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a sub-stituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^{9'}$ is independently —F, —Cl, —Br, or —I.

In embodiments, R$^{9'}$ is independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a sub-stituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where R$^{9'}$ is substituted, R$^{9'}$ is substituted with a substituent group. In embodiments, where R$^{9'}$ is substituted, R$^{9'}$ is substituted with a size-limited substituent group. In embodiments, where R$^{9'}$ is substituted, R$^{9'}$ is substituted with a lower substituent group.

In embodiments, R$^{9'}$ is independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

R$^{10'}$ is independently hydrogen, halogen, —CX$^{10'}_3$, —CHX$^{10'}_2$, —CH$_2$X$^{10'}$, —OCX$^{10'}_3$, —OCHX$^{10'}_2$, —OCH$_2$X$^{10'}$, —CN, —S(O)$_2$R$^{10'A}$, —SR$^{10'A}$, —S(O)R$^{10'A}$, —SO$_2$NR$^{10'A}$R$^{10'B}$, —NHC(O)NR$^{10'A}$R$^{10'B}$, —N(O)$_2$, —NR$^{10'A}$R$^{10'B}$, N—NR$^{10'A}$R$^{10'B}$, —C(O)R$^{10'A}$, —C(O)—OR$^{10'A}$, —C(O)NR$^{10'A}$R$^{10'B}$, —C(O)NHNR$^{10'A}$R$^{10'B}$, —OR$^{10'A}$, —NR$^{10'A}$SO$_2$R$^{10'B}$, —NR$^{10'A}$C(O)R$^{10'B}$, —NR$^{10'A}$C(O)OR$^{10'B}$, —NR$^{10'A}$OR$^{10'B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^{10'}$ is independently —F, —Cl, —Br, or —I.

In embodiments, R$^{10'}$ is independently hydrogen, halogen, (e.g., —F, —Cl, Br, —I), —CX$^{10'}_3$, —CHX$^{10'}_2$, —CH$_2$X$^{10'}$, —OCX$^{10'}_3$, —OCHX$^{10'}_2$, —OCH$_2$X$^{10'}$, —CN, —S(O)$_2$R$^{10'A}$, —SR$^{10'A}$, —S(O)R$^{10'A}$, —SO$_2$NR$^{10'A}$R$^{10'B}$, —NHC(O)NR$^{10'A}$R$^{10'B}$, —N(O)$_2$, —NR$^{10'A}$R$^{10'B}$, —NHNR$^{10'A}$R$^{10'B}$, —C(O)R$^{10'A}$, —C(O)—OR$^{10'A}$, —C(O)NR$^{10'A}$R$^{10'B}$, —C(O)NHNR$^{10'A}$R$^{10'B}$, —OR$^{10'A}$, —NR$^{10'A}$SO$_2$R$^{10'B}$, —NR$^{10'A}$C(O)R$^{10'B}$, —NR$^{10'A}$C(O)OR$^{10'B}$, —NR$^{10'A}$OR$^{10'B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^{10'}$ is independently —F, —Cl, —Br, or —I.

In embodiments, $R^{10'}$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{10'}$ is substituted, $R^{10'}$ is substituted with a substituent group. In embodiments, where $R^{10'}$ is substituted, $R^{10'}$ is substituted with a size-limited substituent group. In embodiments, where $R^{10'}$ is substituted, $R^{10'}$ is substituted with a lower substituent group.

In embodiments, $R^{10'}$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

$R^{8'A}$, $R^{8'B}$, $R^{9'A}$, $R^{9'B}$, $R^{10'A}$ and $R^{10'B}$ are independently hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —C(O)OH, —C(O)$NH_2$, —OH, —$NH_2$, —COOH, —$CONH_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{8'A}$, $R^{8'B}$, $R^{9'A}$, $R^{9'B}$, $R^{10'A}$ and $R^{10'B}$ are independently hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —C(O)OH, —C(O)$NH_2$, —OH, —$NH_2$, —COOH, —$CONH_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, where $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted, R $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted with a substituent group. In embodiments, where $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted, $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted with a size-limited substituent group. In embodiments, where $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted, $R^{6'A}$, $R^{6'B}$, $R^{7'A}$, $R^{7'B}$, $R^{8'A}$, $R^{8'B}$, $R^{9'A}$, $R^{9'B}$, $R^{10'A}$ and $R^{10'B}$ is substituted with a lower substituent group. In embodiments, $R^{6'A}$ is substituted with a substituent group. In embodiments, $R^{6'A}$ is substituted with a size-limited substituent group. In embodiments, $R^{6'A}$ is substituted with a lower substituent group. In embodiments, $R^{6'B}$ is substituted with a substituent group. In embodiments, $R^{6'B}$ is substituted with a size-limited substituent group. In embodiments, $R^{6'B}$ is substituted with a lower substituent group. In embodiments, $R^{7'A}$ is substituted with a substituent group. In embodiments, $R^{7'A}$ is substituted with a size-limited substituent group. In embodiments, $R^{7'A}$ is substituted with a lower substituent group. In embodiments, $R^{7'B}$ is substituted with a substituent group. In embodiments, $R^{7'B}$ is substituted with a size-limited substituent group. In embodiments, $R^{7'B}$ is substituted with a lower substituent group. In embodiments, $R^{8'A}$ is substituted with a substituent group. In embodiments, $R^{8'A}$ is substituted with a size-limited substituent group. In embodiments, $R^{8'A}$ is substituted with a lower substituent group. In embodiments, $R^{8'B}$ is substituted with a substituent group. In embodiments, $R^{8'B}$ is substituted with a size-limited substituent group. In embodiments, $R^{8'B}$ is substituted with a lower substituent group. In embodiments, $R^{9'A}$ is substituted with a substituent group. In embodiments, $R^{9'A}$ is substituted with a size-limited substituent group. In embodiments, $R^{9'A}$ is substituted with a lower substituent group. In embodiments, $R^{9'B}$ is substituted with a substituent group. In embodiments, $R^{9'B}$ is substituted with a size-limited substituent group. In embodiments, $R^{9'B}$ is substituted with a lower substituent group. In embodiments, $R^{10'A}$ is substituted with a substituent group. In embodiments, $R^{10'A}$ is substituted with a size-limited substituent group. In embodiments, $R^{10'A}$ is substituted with a lower substituent group. In embodiments, $R^{10'B}$ is substituted with a substituent group. In embodiments, $R^{1'B}$ is substituted with a size-limited substituent group. In embodiments, $R^{10'B}$ is substituted with a lower substituent group.

In embodiments, $R^{8'A}$, $R^{8'B}$, $R^{9'A}$, $R^{9'B}$, $R^{10'A}$ and $R^{10'B}$ are independently hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

X is —Cl, —Br, —I, —OSO$_2$R$^{15}$ or —OCOR$^{15}$. In embodiments, X is —Cl. In embodiments, X is —Br. In embodiments, X is —I. In embodiments, X is —OSO$_2$R$^{15}$. In embodiments, X is —OCOR$^5$.

$R^{15}$ is a substituted or unsubstituted alkyl, substituted or unsubstituted aryl, or substituted or unsubstituted heteroaryl.

In embodiments, $R^{15}$ is substituted or unsubstituted alkyl. In embodiments, $R^{15}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{15}$ is an unsubstituted alkyl (e.g., $C_1$-$C_8$, $C_1$-$C_6$, or $C_1$-$C_4$). In embodiments, where $R^{15}$ is substituted, $R^{15}$ is substituted with a substituent group. In embodiments, where $R^{15}$ is substituted, $R^{15}$ is substituted with a size-limited substituent group. In embodiments, where $R^{15}$ is substituted, $R^{15}$ is substituted with a lower substituent group.

In embodiments, $R^{15}$ is substituted or unsubstituted aryl. In embodiments, $R^{15}$ is a substituted (e.g., substituted with a substituent group, a size-limited substituent group, or lower substituent group) or unsubstituted aryl (e.g., $C_6$-$C_{10}$, $C_6$, or phenyl). In embodiments, $R^{15}$ is an unsubstituted aryl (e.g., $C_6$-$C_{10}$, $C_6$, or phenyl). In embodiments, where $R^{15}$ is substituted, $R^{15}$ is substituted with a substituent group. In embodiments, where $R^{15}$ is substituted, $R^{15}$ is substituted with a size-limited substituent group. In embodiments, where $R^{15}$ is substituted, $R^{15}$ is substituted with a lower substituent group.

In embodiments, $R^{15}$ is substituted or unsubstituted heteroaryl. In embodiments, $R^{15}$ is substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{15}$ is an unsubstituted heteroaryl (e.g., 5 to 10 membered, 5 to 9 membered, or 5 to 6 membered). In embodiments, where $R^{15}$ is substituted, $R^{15}$ is substituted with a substituent group. In embodiments, where $R^{15}$ is substituted, $R^{15}$ is substituted with a size-limited substituent group. In embodiments, where $R^{15}$ is substituted, $R^{15}$ is substituted with a lower substituent group.

$R^{16}$ is hydrogen, —OH, —C(O)R$^{16A}$, substituted or unsubstituted alkyl, substituted or unsubstituted aryl, or substituted or unsubstituted heteroaryl.

In embodiments, $R^{16}$ is hydrogen. In embodiments, $R^{16}$ is —OH. In embodiments, $R^{16}$ is —C(O)R$^{16A}$. In embodiments, $R^{16A}$ is hydrogen or substituted or unsubstituted alkyl. In embodiments, $R^{16A}$ is hydrogen. In embodiments, $R^{16A}$ is substituted or unsubstituted alkyl. In embodiments, $R^{16A}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16A}$ is an unsubstituted alkyl (e.g., $C_1$-$C_8$, $C_1$-$C_6$, or $C_1$-$C_4$).

In embodiments, $R^{16}$ is substituted or unsubstituted alkyl. In embodiments, $R^{16}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16}$ is an unsubstituted alkyl (e.g., $C_1$-$C_8$, $C_1$-$C_6$, or $C_1$-$C_4$). In embodiments, where $R^{16}$ is substituted, $R^{16}$ is substituted with a substituent group. In embodiments, where $R^{16}$ is substituted, $R^{16}$ is substituted with a size-limited substituent group. In embodiments, where $R^{16}$ is substituted, $R^{16}$ is substituted with a lower substituent group.

In embodiments, $R^{16}$ is substituted or unsubstituted aryl. In embodiments, $R^{16}$ is a substituted (e.g., substituted with a substituent group, a size-limited substituent group, or lower substituent group) or unsubstituted aryl (e.g., $C_6$-$C_{10}$, $C_6$, or phenyl). In embodiments, $R^{16}$ is an unsubstituted aryl (e.g., $C_6$-$C_{10}$, $C_6$, or phenyl). In embodiments, where $R^{16}$ is substituted, $R^{16}$ is substituted with a substituent group. In embodiments, where $R^{16}$ is substituted, $R^{16}$ is substituted with a size-limited substituent group. In embodiments, where $R^{16}$ is substituted, $R^{16}$ is substituted with a lower substituent group.

In embodiments, $R^{16}$ is substituted or unsubstituted heteroaryl. In embodiments, $R^{16}$ is substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{16}$ is an unsubstituted heteroaryl (e.g., 5 to 10 membered, 5 to 9 membered, or 5 to 6 membered). In embodiments, where $R^{16}$ is substituted, $R^{16}$ is substituted with a substituent group. In embodiments, where $R^{16}$ is substituted, $R^{16}$ is substituted with a size-limited substituent group. In embodiments, where $R^{16}$ is substituted, $R^{16}$ is substituted with a lower substituent group.

$R^{17}$ is hydrogen, —OH, —C(O)R$^{17A}$, substituted or unsubstituted alkyl, substituted or unsubstituted aryl, or substituted or unsubstituted heteroaryl, and $R^{17A}$ is hydrogen or substituted or unsubstituted alkyl.

In embodiments, $R^{17}$ is hydrogen. In embodiments, $R^{17}$ is —OH. In embodiments, $R^{17}$ is —C(O)$R^{17A}$. In embodiments, $R^{17A}$ is hydrogen or substituted or unsubstituted alkyl. In embodiments, $R^{17A}$ is hydrogen. In embodiments, $R^{17A}$ is substituted or unsubstituted alkyl. In embodiments, $R^{17A}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{17A}$ is an unsubstituted alkyl (e.g., $C_1$-$C_8$, $C_1$-$C_6$, or $C_1$-$C_4$).

In embodiments, $R^{17}$ is substituted or unsubstituted alkyl. In embodiments, $R^{17}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{17}$ is an unsubstituted alkyl (e.g., $C_1$-$C_8$, $C_1$-$C_6$, or $C_1$-$C_4$). In embodiments, where $R^{17}$ is substituted, $R^{17}$ is substituted with a substituent group. In embodiments, where $R^{17}$ is substituted, $R^{17}$ is substituted with a size-limited substituent group. In embodiments, where $R^{17}$ is substituted, $R^{17}$ is substituted with a lower substituent group.

In embodiments, $R^{17}$ is substituted or unsubstituted aryl. In embodiments, $R^{17}$ is a substituted (e.g., substituted with a substituent group, a size-limited substituent group, or lower substituent group) or unsubstituted aryl (e.g., $C_6$-$C_{10}$, $C_6$, or phenyl). In embodiments, $R^{17}$ is an unsubstituted aryl (e.g., $C_6$-$C_{10}$, $C_6$, or phenyl). In embodiments, where $R^{17}$ is substituted, $R^{17}$ is substituted with a substituent group. In embodiments, where $R^{17}$ is substituted, $R^{17}$ is substituted with a size-limited substituent group. In embodiments, where $R^{17}$ is substituted, $R^{17}$ is substituted with a lower substituent group.

In embodiments, $R^{17}$ is substituted or unsubstituted heteroaryl. In embodiments, $R^{17}$ is substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{17}$ is an unsubstituted heteroaryl (e.g., 5 to 10 membered, 5 to 9 membered, or 5 to 6 membered). In embodiments, where $R^{17}$ is substituted, $R^{17}$ is substituted with a substituent group. In embodiments, where $R^{17}$ is substituted, $R^{17}$ is substituted with a size-limited substituent group. In embodiments, where $R^{17}$ is substituted, $R^{17}$ is substituted with a lower substituent group.

In embodiments, n1' and n2' are each an integer from 0 to 5, wherein the sum of n1' and n2' is at least 1 and not more than 6. In embodiments, n1' is 0 and n2' is 1. In embodiments, n1' is 0 and n2' is 2. In embodiments, n1' is 0 and n2' is 3. In embodiments, n1' is 0 and n2' is 4. In embodiments, n1' is 0 and n2' is 5. In embodiments, n1' is 0 and n2' is 6. In embodiments, n1' is 1 and n2' is 0. In embodiments, n1' is 1 and n2' is 1. In embodiments, n1' is 1 and n2' is 2. In embodiments, n1' is 1 and n2' is 3. In embodiments, n1' is 1 and n2' is 4. In embodiments, n1' is 1 and n2' is 5. In embodiments, n1' is 2 and n2' is 0. In embodiments, n1' is 2 and n2' is 1. In embodiments, n1' is 2 and n2' is 2. In embodiments, n1' is 2 and n2' is 3. In embodiments, n1' is 2 and n2' is 4. In embodiments, n3' is 1 and n2' is 0. In embodiments, n1' is 3 and n2' is 1. In embodiments, n1' is 3 and n2' is 2. In embodiments, n1' is 3 and n2' is 3. In embodiments, n1' is 4 and n2' is 0. In embodiments, n1' is 4 and n2' is 1. In embodiments, n1' is 4 and n2' is 2. In embodiments, n1' is 5 and n2' is 0. In embodiments, n1' is 5 and n2' is 1. In embodiments, n1' is 6 and n2' is 0.

In embodiments, n3' is an integer from 0 to 5. In embodiments, n3' is 0. In embodiments, n3' is 1. In embodiments, n3' is 2. In embodiments, n3' is 3. In embodiments, n3' is 4. In embodiments, n3' is 5.

In embodiments, $L^{1'}$ is $C(R^{4'})_2$, wherein $R^{4'}$ is as described above, including embodiments.

In embodiments, $L^{2'}$ is $C(R^{5'})_2$, wherein $R^{5'}$ is as described above, including embodiments.

In embodiments, $L^{3'}$ is O or $NR^{20'}$. In embodiments, $L^{3'}$ is O. In embodiments, $L^{3'}$ is $NR^{20'}$, wherein $R^{20'}$ is as described above, including embodiments.

In embodiments, $L^{4'}$ is O or $NR^{20'}$. In embodiments, $L^{4'}$ is O. In embodiments, $L^{4'}$ is $NR^{20'}$, wherein $R^{20'}$ is as described above, including embodiments.

In embodiments, $X^{1'}$ is —F, —Cl, —Br, or —I. In embodiments, $X^{1'}$ is —F. In embodiments, $X^{1'}$ is —Cl. In embodiments, $X^{1'}$ is —Br. In embodiments, $X^{1'}$ is —I.

In embodiments, $X^{2'}$ is —F, —Cl, —Br, or —I. In embodiments, $X^{2'}$ is —F. In embodiments, $X^{2'}$ is —Cl. In embodiments, $X^{2'}$ is —Br. In embodiments, $X^{2'}$ is —I.

In embodiments, $X^{3'}$ is —F, —Cl, —Br, or —I. In embodiments, $X^{3'}$ is —F. In embodiments, $X^{3'}$ is —Cl. In embodiments, $X^{3'}$ is —Br. In embodiments, $X^{3'}$ is —I.

In embodiments, $X^{4'}$ is —F, —Cl, —Br, or —I. In embodiments, $X^{4'}$ is —F. In embodiments, $X^{4'}$ is —Cl. In embodiments, $X^{4'}$ is —Br. In embodiments, $X^{4'}$ is —I.

In embodiments, $X^{5'}$ is —F, —Cl, —Br, or —I. In embodiments, $X^{5'}$ is —F. In embodiments, $X^{5'}$ is —Cl. In embodiments, $X^{5'}$ is —Br. In embodiments, $X^{5'}$ is —I.

In embodiments, $X^{6'}$ is —F, —Cl, —Br, or —I. In embodiments, $X^{6'}$ is —F. In embodiments, $X^{6'}$ is —Cl. In embodiments, $X^{6'}$ is —Br. In embodiments, $X^{6'}$ is —I.

In embodiments, $X^{7'}$ is —F, —Cl, —Br, or —I. In embodiments, $X^{7'}$ is —F. In embodiments, $X^{7'}$ is —Cl. In embodiments, $X^{7'}$ is —Br. In embodiments, $X^{7'}$ is —I.

In embodiments, $X^{8'}$ is —F, —Cl, —Br, or —I. In embodiments, $X^{8'}$ is —F. In embodiments, $X^{8'}$ is —Cl. In embodiments, $X^{8'}$ is —Br. In embodiments, $X^{8'}$ is —I.

In embodiments, $X^{9'}$ is —F, —Cl, —Br, or —I. In embodiments, $X^{9'}$ is —F. In embodiments, $X^{9'}$ is —Cl. In embodiments, $X^{9'}$ is —Br. In embodiments, $X^{9'}$ is —I.

In embodiments, $X^{10'}$ is —F, —Cl, —Br, or —I. In embodiments, $X^{10'}$ is —F. In embodiments, $X^{10'}$ is —Cl. In embodiments, $X^{10'}$ is —Br. In embodiments, $X^{10'}$ is —I.

Compounds

The synthetic methods provided herein can be used for synthesis of the compounds having structural formula (V):

(V)

or a pharmaceutically acceptable salt thereof. $X^1$ is $CR^8$ or N. $X^2$ is $CR^9$ or N. $X^3$ is $CR^{10}$ or N. The symbols n1, n2, n3, n4, n5, n6, n7, n8, n9, n10, and n44 are independently an integer from 0 to 4. The symbols m1, m2, m3, m4, m5, m6, m7, m8, m9, m10, v1, v2, v3, v4, v5, v6, v7, v8, v9, v10, and v44 are independently 1 or 2. The symbol z1 is an integer from 0 to 5. The symbol z2 is an integer from 0 to 5. The symbol z3 is an integer from 0 to 11. The symbol z4 is an integer from 0 to 2. $L^7$ is a substituted or unsubstituted cycloalkylene. $R^1$ is hydrogen, halogen, $-CX^{1.1}_3$, $-CHX^{1.1}_2$, $-CH_2X^{1.1}$, $-CN$, $-N_3$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, $-OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-CX^{2.1}_3$, $-CHX^{2.1}_2$, $-CH_2X^{2.1}$, $-CN$, $-N_3$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, $-OCH_2X^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently halogen, $-CX^{3.1}_3$, $-CHX^{3.1}_2$, $-CH_2X^{3.1}$, $-CN$, $-N_3$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ is hydrogen, halogen, $-CX^{4.1}_3$, $-CHX^{4.1}_2$, $-CH_2X^{4.1}$, $-CN$, $-N_3$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, $-OCH_2X^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; when $X^2$ is $CR^9$, then $R^4$ and $R^9$ may optionally be joined to form a substituted or unsubstituted cycloalkyl, substituted or unsubstituted heterocycloalkyl, or unsubstituted aryl, or substituted or unsubstituted heteroaryl. $R^5$ is independently halogen, oxo, $-CX^{5.1}_3$, $-CHX^{5.1}_2$, $-CH_2X^{5.1}$, $-CN$, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}_3$, $-OCHX^{5.1}_2$, $-OCH_2X^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is independently halogen, oxo, $-CX^{6.1}_3$, $-CHX^{6.1}_2$, $-CH_2X^{6.1}$, $-CN$, $-N_3$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, $-OCH_2X^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^7$ is hydrogen, halogen, $-CX^{7.1}_3$, $-CHX^{7.1}_2$, $-CH_2X^{7.1}$, $-CN$, $-N_3$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$, $-OCH_2X^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^8$ is hydrogen, halogen, $-CX^{8.1}_3$, $-CHX^{8.1}_2$, $-CH_2X^{8.1}$, $-CN$, $-N_3$, $-SO_{18}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, $-OCH_2X^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-N_3$, $-SO_{n9}R^{9A}$, $-SO_{v9}NR^{9B}R^{9C}$, $-NHNR^{9B}R^{9C}$, $-ONR^{9B}R^{9C}$, $NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, $-OCH_2X^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; when $X^2$ is $CR^9$, then $R^4$ and $R^9$ may optionally be joined to form a substituted or unsubstituted cycloalkyl, substituted or unsubstituted heterocycloalkyl, or substituted or unsubstituted aryl, or substituted or unsubstituted heteroaryl; or when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n10}R^{10A}$, $-SO_{v10}NR^{10B}R^{10C}$, $-NHNR^{1B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{1B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, $-OCH_2X^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, or unsubstituted aryl, or substituted or unsubstituted heteroaryl. $R^{44}$ is hydrogen, $-CX^{44.1}_3$, $-CHX^{44.1}_2$, $-CH_2X^{44.1}$, $-SO_{n44}R^{44A}$, $-SO_{v44}NR^{44B}R^{44C}$, $-C(O)R^{44D}$, $-C(O)OR^{44D}$, $-C(O)NR^{44B}R^{44C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{7.2B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{44A}$, $R^{44B}$, $R^{44C}$ and $R^{44D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{44B}$, and $R^{44C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, and $X^{44.1}$ are independently —Cl, —Br, —I or —F, wherein at least one of $X^1$, $X^2$ and $X^3$ is N.

The methods described herein can be used for synthesis of a class of C—C chemokine receptor 4 (CCR4) inhibitors/antagonists, or intermediates and precursors thereof, described in U.S. Pat. No. 10,683,280 issued Jun. 16, 2020 to Jackson et al., the disclosure of which is incorporated herein by reference. These compounds having structural formula (VI):

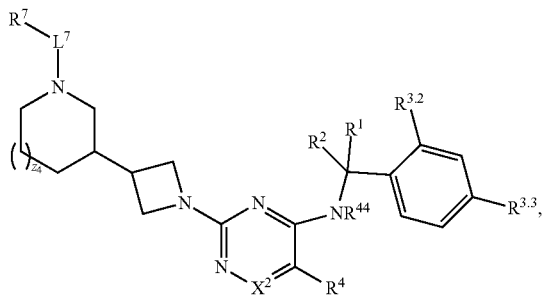

(VI)

or a pharmaceutically acceptable salt thereof, wherein $R^1$, $R^2$, $R^4$, $R^{44}$, $X^2$, z4, $L^7$, and $R^7$ as described herein, including embodiments. $R^{3.2}$ and $R^{3.3}$ are independently substituents encompassed by the definitions of $R^3$. In embodiments, $R^{3.2}$ is hydrogen, halogen, —$CX^{3.2}_3$, —$CHX^{3.2}_2$, —$CH_2X^{3.2}$, —CN, —$N_3$, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —NHC(O)$NHNR^{3.2B}R^{3.2C}$, —NHC(O)$NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}_3$, —$OCHX^{3.2}_2$, —$OCH_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3.3}$ is hydrogen, halogen, —$CX^{3.3}_3$, —$CHX^{3.3}_2$, —$CH_2X^{3.3}$, —CN, —$N_3$, —$SO_{n3.3}R^{3.3A}$, —$SO_{v3.3}NR^{3.3B}R^{3.3C}$, —$NHNR^{3.3B}R^{3.3C}$, —$ONR^{3.3B}R^{3.3C}$, —NHC(O)$NHNR^{3.3B}R^{3.3C}$, —NHC(O)$NR^{3.3B}R^{3.3C}$, —$N(O)_{m3.3}$, —$NR^{3.3B}R^{3.3C}$, —$C(O)R^{3.3D}$, —$C(O)OR^{3.3D}$, —$C(O)NR^{3.3B}R^{3.3C}$, —$OR^{3.3A}$, —$NR^{3.3B}SO_2R^{3.3A}$, —$NR^{3.3B}C(O)R^{3.3D}$, —$NR^{3.3B}C(O)OR^{3.3D}$, —$NR^{3.3B}OR^{3.3D}$, —$OCX^{3.3}_3$, —$OCHX^{3.3}_2$, —$OCH_2X^{3.3}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n3.2, and n3.3 are independently an integer from 0 to 4. The symbols m3.2, m3.3, v3.2 and v3.3 are independently 1 or 2. In embodiments, $R^4$ is hydrogen, —$CX^{4.1}_3$, —CN, —C(O)$NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3.2A}$, $R^{3.2B}R^{3.2C}$, $R^{3.2D}$, $R^{3.3A}$, $R^{3.3B}$, $R^{3.3C}$, and $R^{3.3D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3.2B}$, $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl; and $X^{3.2}$ and $X^{3.3}$ are independently —Cl, —Br, —I or —F.

The methods described herein can be used to synthesize trans isomeric forms of the compounds of formula (VI) having an $L^7$ moiety which is a substituted or unsubstituted cycloalkylene and an $R^7$ moiety which is a carboxylic acid or carboxylic acid-like moiety, for example —$C(O)OR^{7D}$, —$CH_2C(O)OR^{7D}$ or —$NHC(O)OR^{7D}$, where $R^{7D}$ is selected from hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the methods described herein can be used to synthesize the compounds of formula (VI) having an $L^7$ moiety which is a substituted or unsubstituted $C_3$-$C_8$ cycloalkylene. In certain embodiments, the methods described herein can be used to synthesize the compounds of formula (VI) having an $L^7$ moiety which is a substituted or unsubstituted $C_4$-$C_6$ cycloalkylene. In other embodiments, the methods described herein can be used to synthesize the compounds of formula (VI) having an $L^7$ moiety which is a substituted or unsubstituted cyclobutylene.

In embodiments, the methods described herein can be used to synthesize the compounds of formula (VI) having one of the above-described $L^7$ moieties and an $R^7$ moiety, which is —C(O)OH, —C(O)$OCH_3$, —C(O)$OCH_2CH_3$, —$CH_2C(O)OH$, —NHC(O)OH, —NHC(O)$OCH_3$, —NHC(O)$OCH_2CH_3$, —$CH_2C(O)OH$, —$CH_2C(O)OCH_3$, or —$CH_2C(O)OCH_2CH_3$.

In certain embodiments, the methods described herein can be used to synthesize the compounds of formula (VI) having one of the above-described $L^7$ moieties and an $R^7$ moiety which is —C(O)OH.

In embodiments, the methods described herein can be used to synthesize the compounds of formula (VI) having one of the above-described $L^7$ moieties and $R^7$ moieties, and having one or more of the following: z4 is 1, z3 is 0 and/or z2 is 0.

In embodiments, the methods described herein can be used to synthesize the compounds of formula (VII):

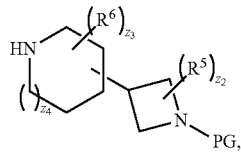

wherein z2, z3, z4, R⁵, and R⁶ are as described herein, including embodiments.

A skilled artisan will recognize that the above-described class of the compounds having 5 or more rings are typically synthesized using multiple steps, wherein intermediates are used as building blocks to make the final CCR4 inhibitor/antagonist. In such a synthetic approach, the step of synthesizing the desired trans isomer, in high trans isomeric purity, using a carboxylic acid directed reducing agent is typically performed on an intermediate or precursor of the final CCR4 inhibitor/antagonist. So the step of synthesizing the desired trans isomer, in high trans isomeric purity, using a carboxylic acid directed reducing agent is typically only used to synthesize an intermediate or precursor compound resembling the following moiety, potentially with additional blocking and/or leaving moieties attached, and not necessarily the remaining portions of the final CCR4 inhibitor/antagonist:

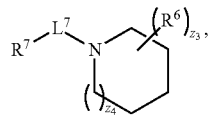

wherein L⁷, R⁶, R⁷, z3 and z4 are as described herein, including embodiments.

In embodiments, the methods described herein can be used to synthesize the compounds of the following structure:

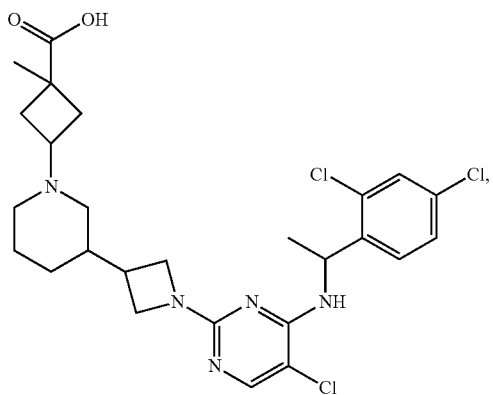

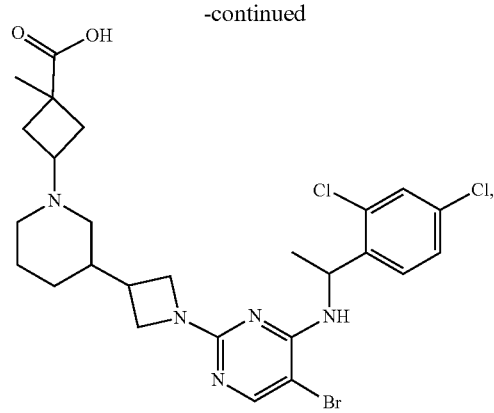

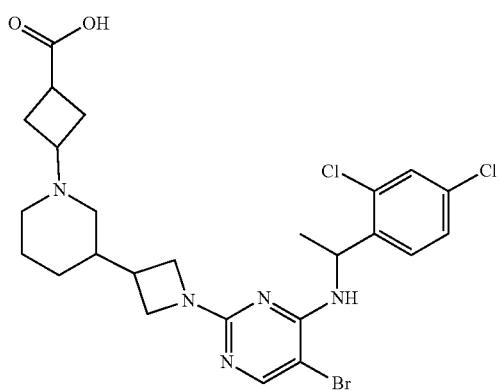

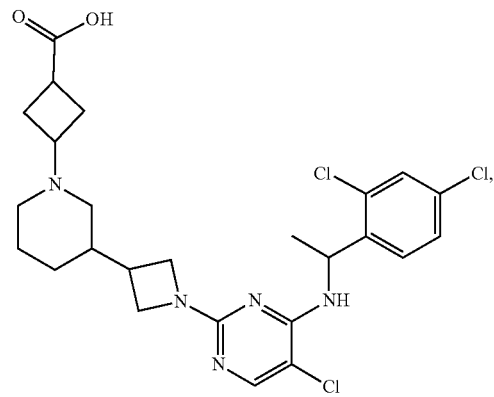

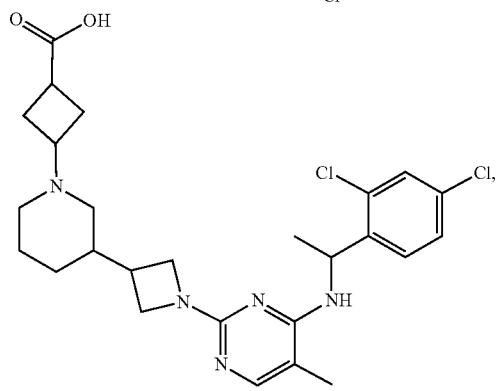

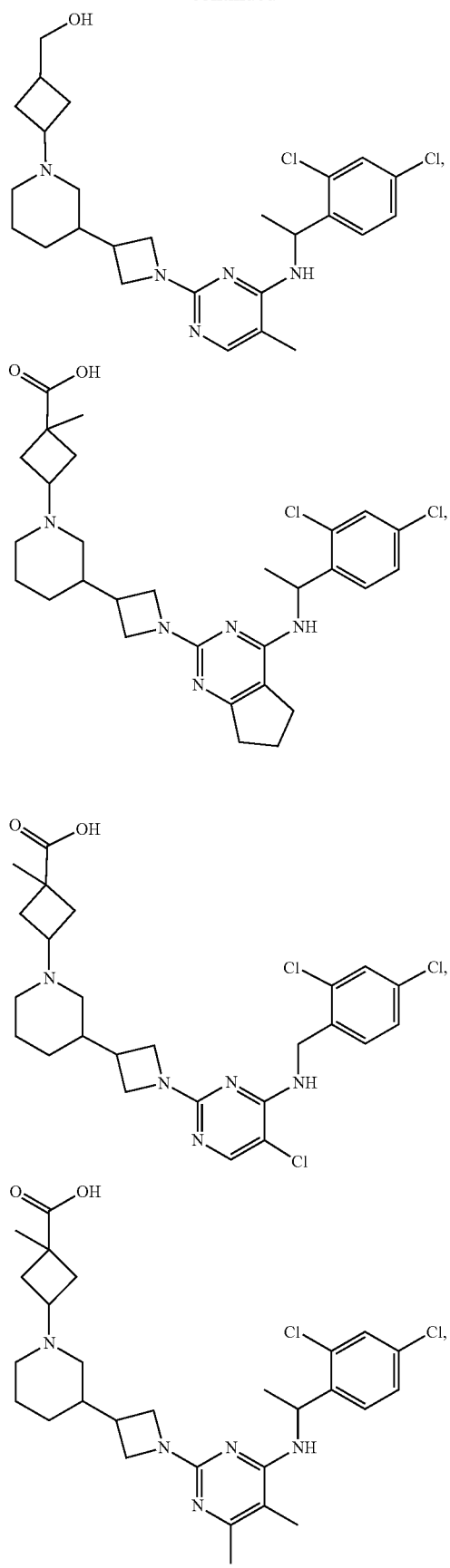
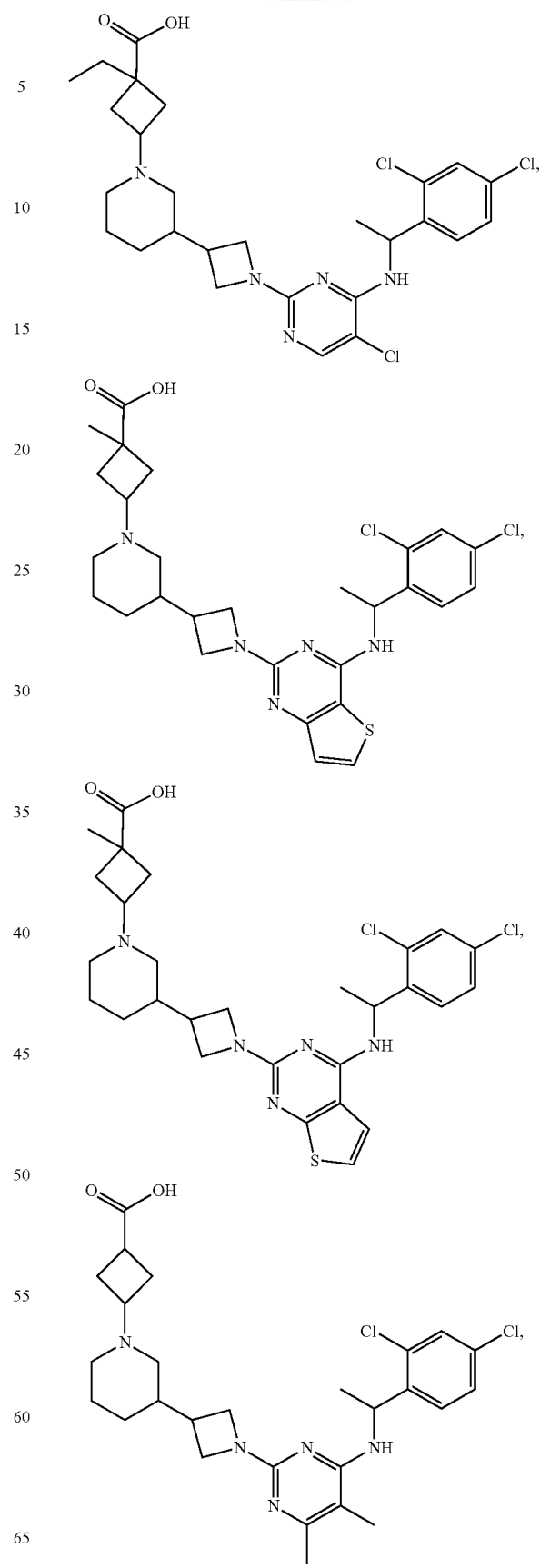

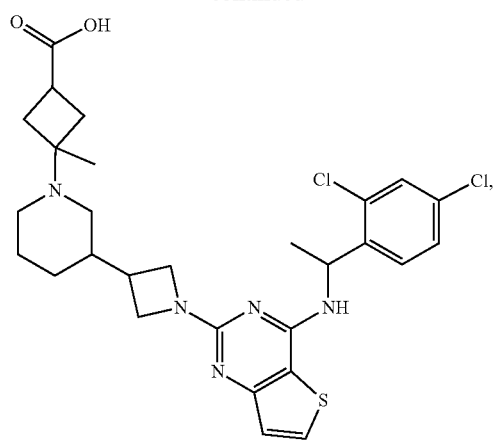
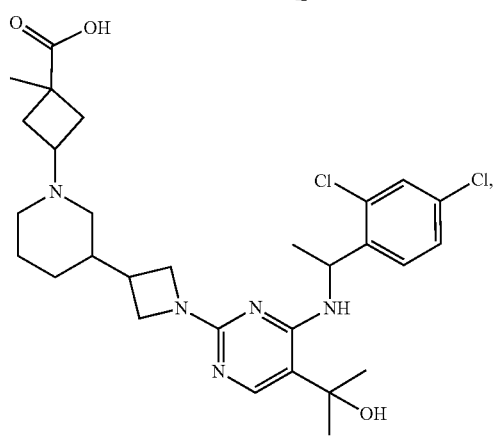
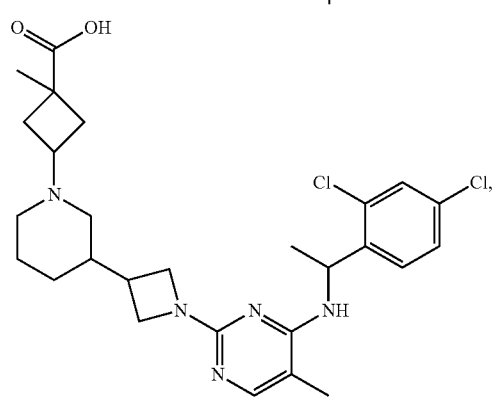
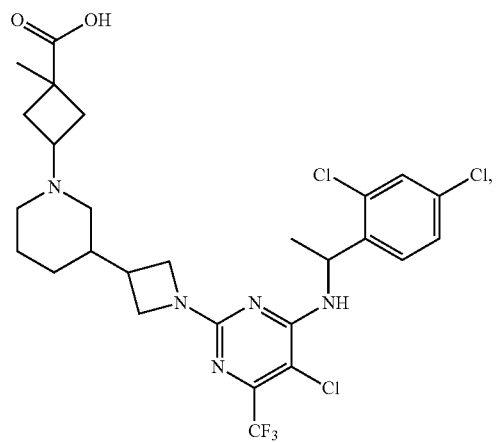
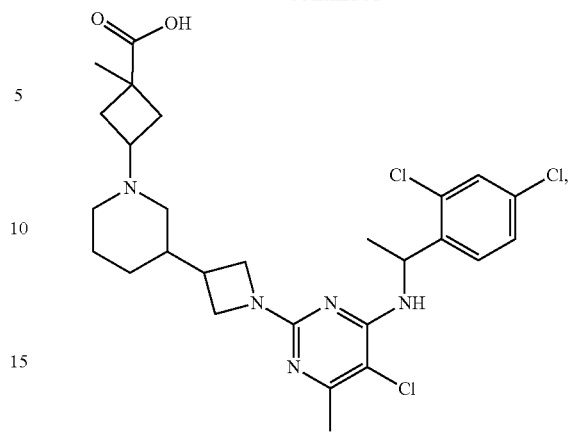
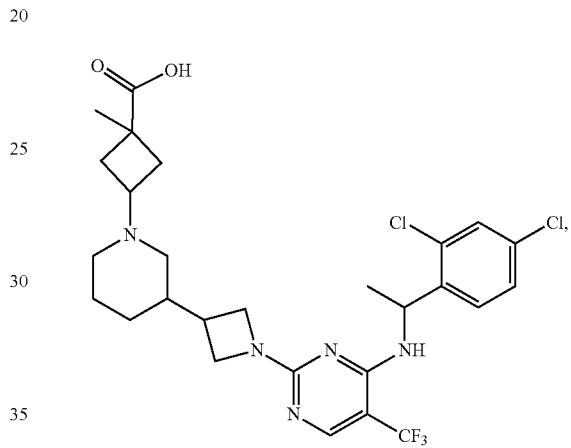
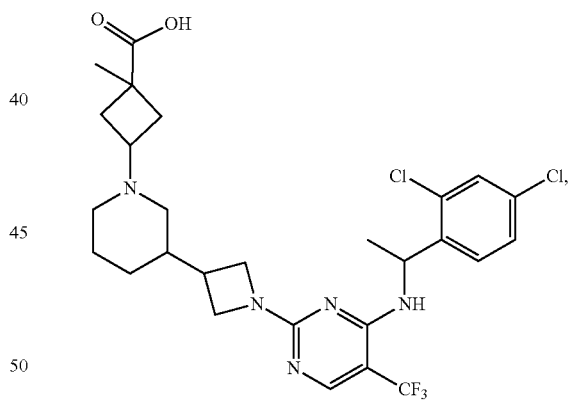
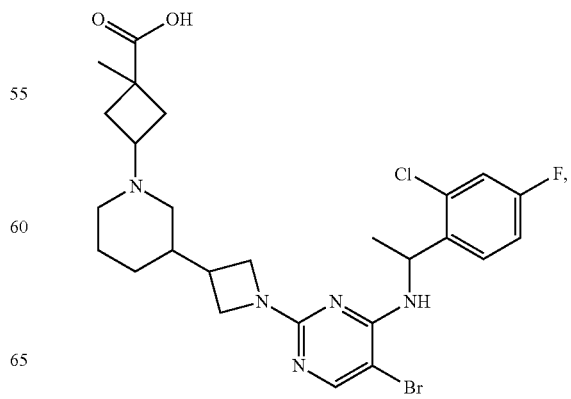

-continued
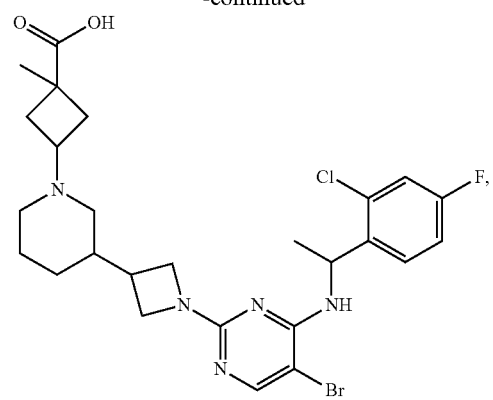
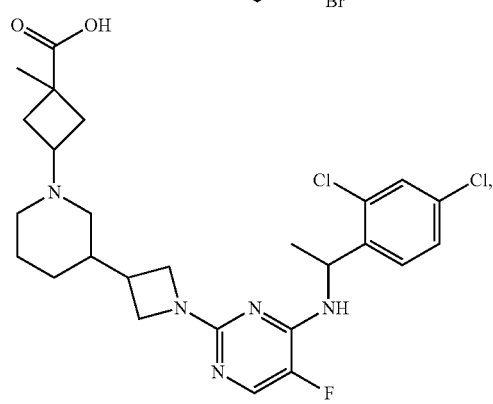
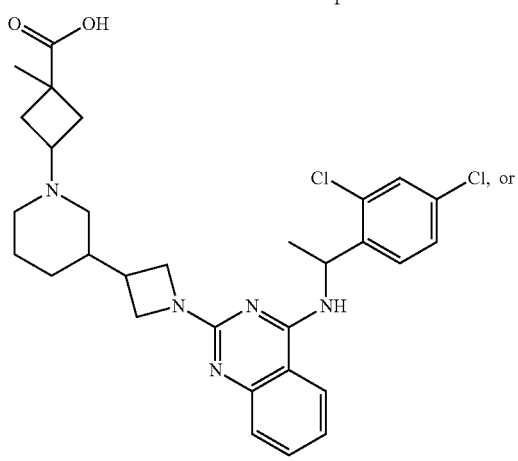
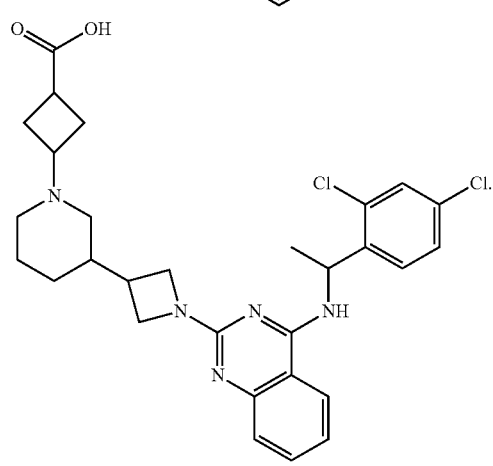
In embodiments, the compound of formula:
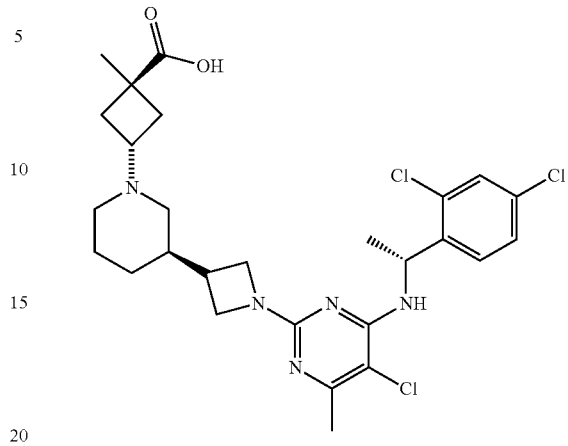
is formed by reacting the compound of formula (III) with the compound of formula:
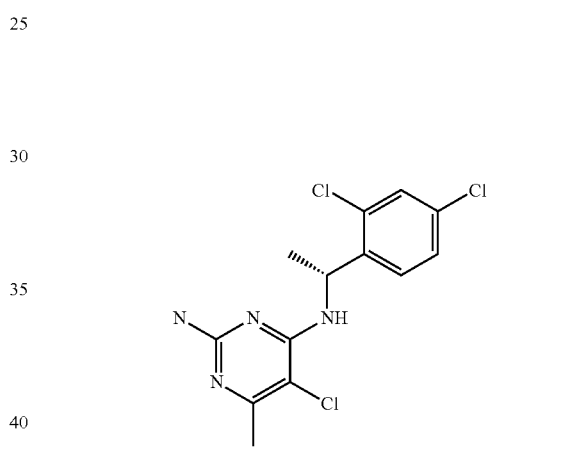
in the presence of tBuOH, H₂O and a base.
In embodiments, the compound of formula:
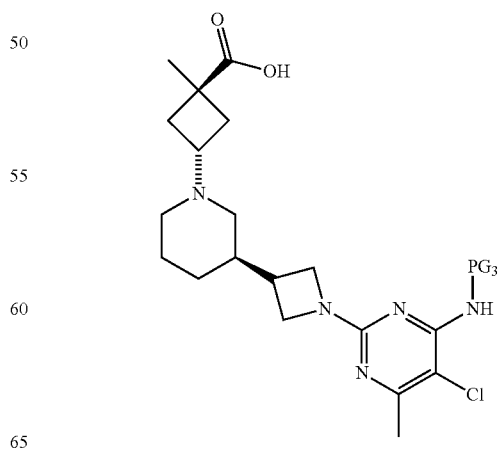

is formed by reacting the compound of formula (III) with the compound of formula:

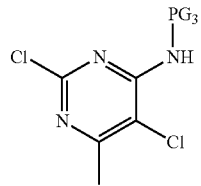

in the presence of tBuOH, H₂O and a base.

In embodiments, the compound of formula:

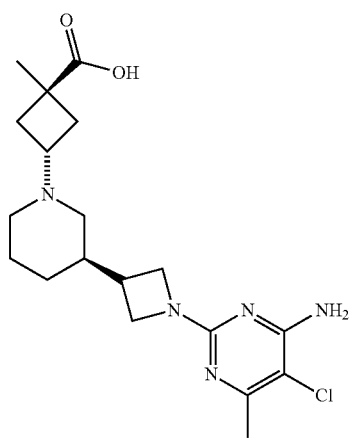

is formed by removal of a protecting group PG₃ from the compound of formula:

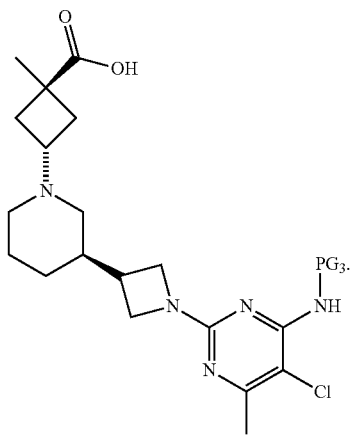

In embodiments, the compound of formula:

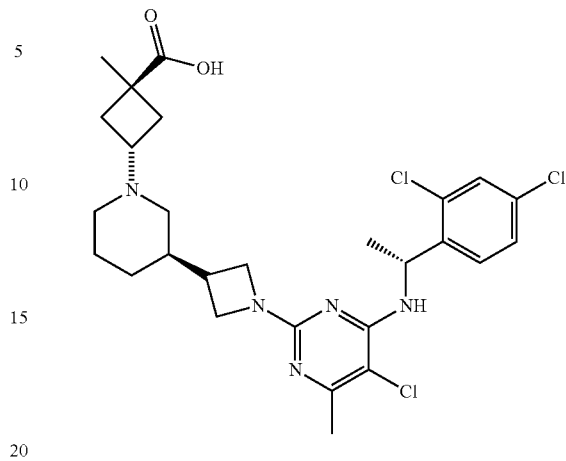

is formed by reacting the compound of formula:

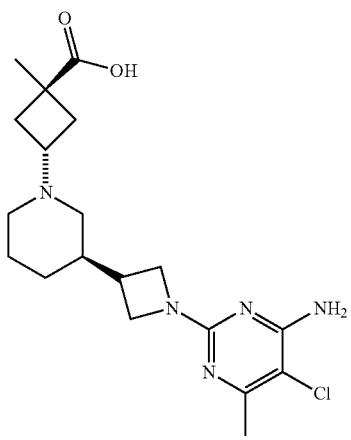

with the compound of formula:

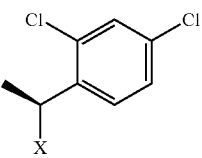

in the presence of a base and a solvent, wherein X is —Cl, —Br, —I, —OSO₂R¹⁵ or —OCOR¹⁵, and wherein R¹⁵ is a substituted or unsubstituted alkyl, substituted or unsubstituted aryl, or substituted or unsubstituted heteroaryl.

In embodiments, the compound of formula:

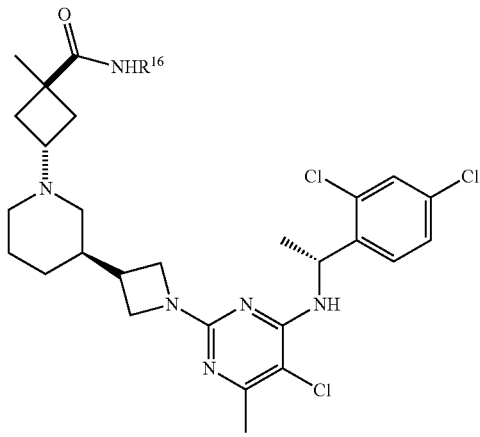

is formed by reacting the compound of formula:

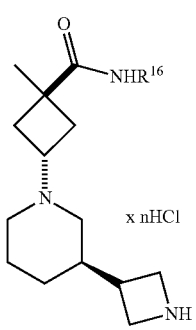

with the compound of formula:

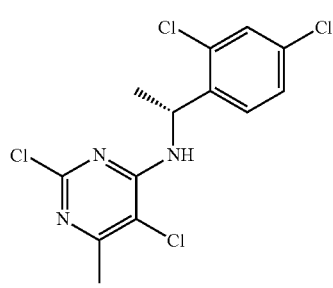 [SMILES: Cc1nc(Cl)nc(N[C@H](C)c2ccc(Cl)cc2Cl)c1Cl]

in the presence of a base and a solvent, wherein n is an integer from 0 to 5, and $R^{16}$ is hydrogen, —OH, —C(O)$R^{16A}$, substituted or unsubstituted alkyl, substituted or unsubstituted aryl, or substituted or unsubstituted heteroaryl, and wherein $R^{16A}$ is hydrogen or substituted or unsubstituted alkyl.

In embodiments, the compound of formula:

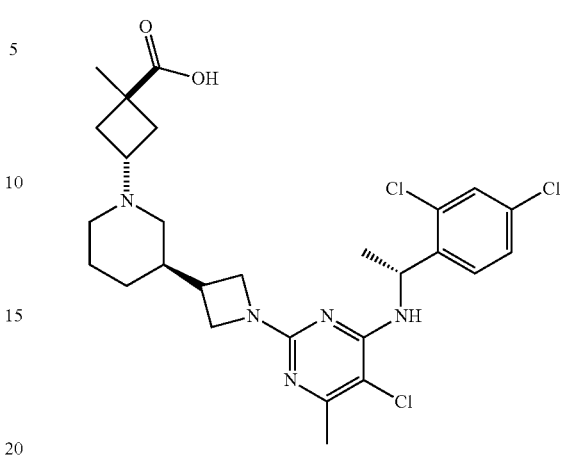

is formed by hydrolysis of the —C(O)NH$R^{16}$ moiety.

In embodiments, the compound of formula:

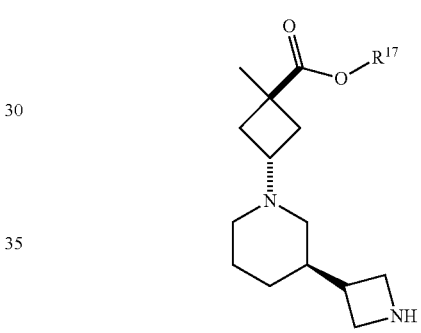

is formed by hydrolysis of the compound of formula:

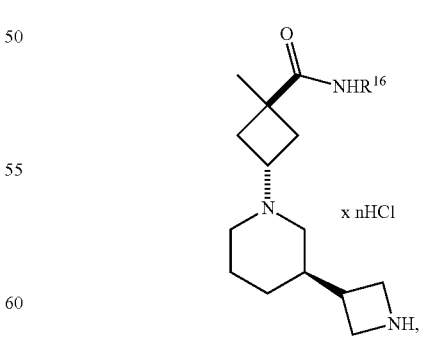

wherein $R^{17}$ is hydrogen, —OH, —C(O)$R^{17A}$, substituted or unsubstituted alkyl, substituted or unsubstituted aryl, or substituted or unsubstituted heteroaryl, and $R^{17A}$ is hydrogen or substituted or unsubstituted alkyl.

In embodiments, the compound of formula:

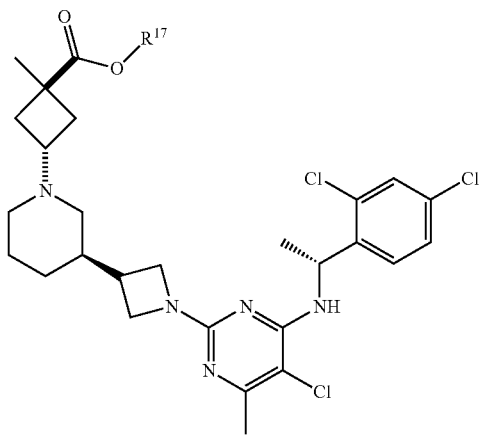

is formed by reacting the compound of formula:

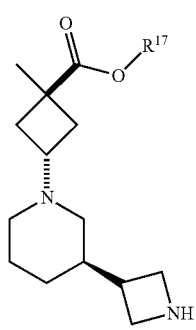

with the compound of formula:

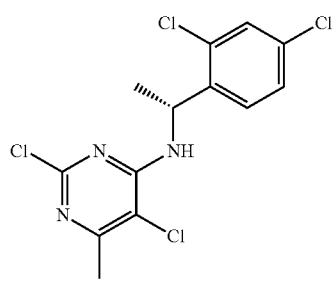 [SMILES: Cc1nc(Cl)nc(N[C@H](C)c2ccc(Cl)cc2Cl)c1Cl]

in the presence of a base and a solvent.

In embodiments, the compound of formula:

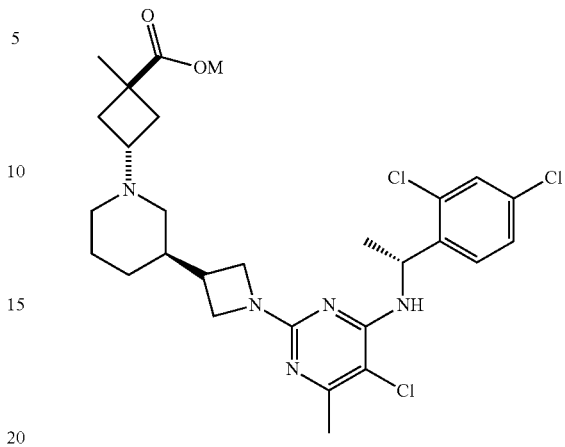

is formed by reacting the compound of formula:

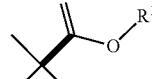

with a base of the formula M(OH)$_{n3'}$ in the presence of an organic solvent, wherein M is Li, Na, K, Cs, Ba, Ca, Mg, Be, Rb, or Sr, and n3' is an integer from 1 to 2.

In embodiments, the compound of formula:

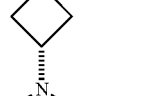

is formed by reacting the compound of formula (I):

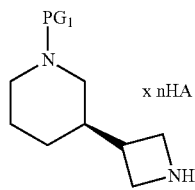

with the compound of formula:

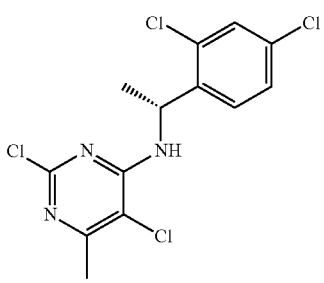 [SMILES: Cc1nc(Cl)nc(N[C@H](C)c2ccc(Cl)cc2Cl)c1Cl]

in the presence of a solvent and a base, wherein $PG_1$ is a protecting group, and wherein n is an integer from 0 to 5.

In embodiments, the compound of formula:

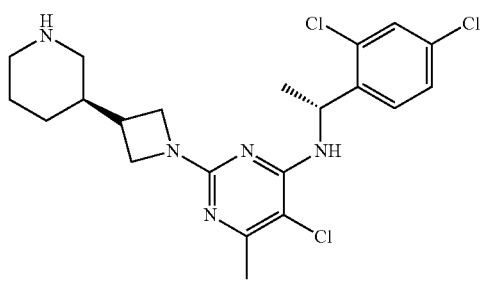 [SMILES: Cc1nc(N2CC([C@H]3CCCNC3)C2)nc(N[C@H](C)c2ccc(Cl)cc2Cl)c1Cl]

is formed by removal of the protecting group $PG_1$ from the compound of formula:

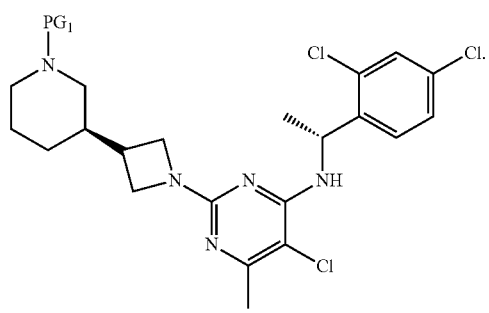

In embodiments, the compound of formula:

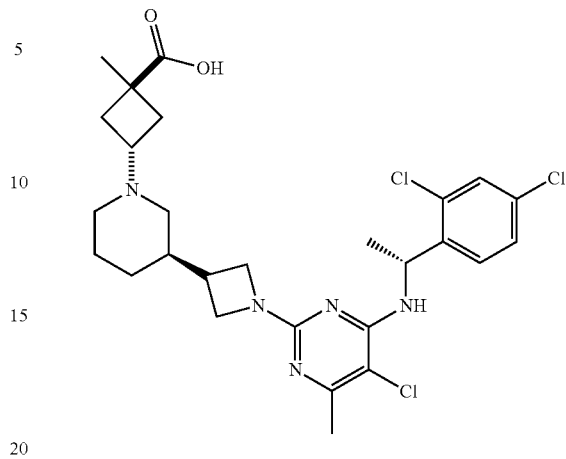

is formed by reacting the compound of formula:

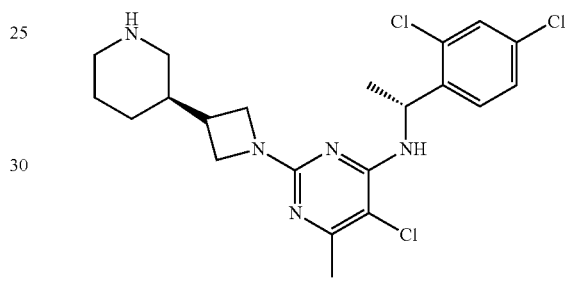

with the compound of formula (II) in the presence of a 1,4-dihydropyridine and toluene.

In embodiments, the compound of formula:

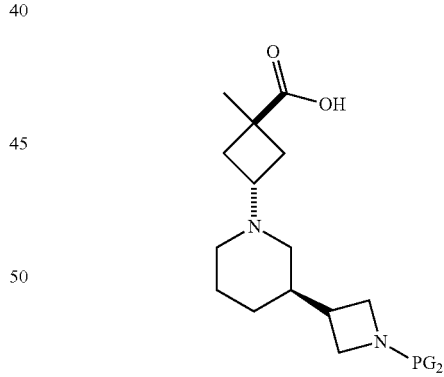

is formed by reacting the compound of formula:

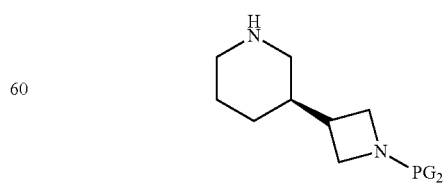

with the compound of formula (II) in the presence of a 1,4-dihydropyridine, wherein $PG_2$ is a protecting group.

In embodiments, the compound of formula:

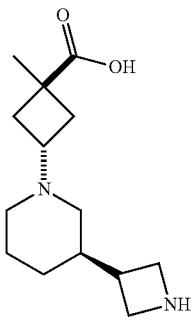

is formed by removal of the protecting group PG$_2$ from the compound of formula:

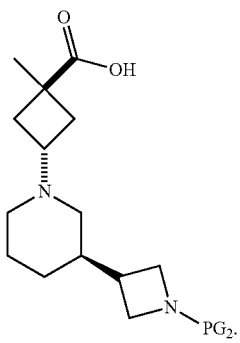

In embodiments, the compound is useful as a comparator compound. In embodiments, the comparator compound can be used to assess the activity of a test compound in an assay (e.g., an assay as described herein, for example in the examples section, figures, or tables).

EXAMPLES

General Synthetic Procedures

Reductive amination of intermediate compounds used to synthesize trans isomeric forms of G protein-coupled receptor modulators can be performed using either of the following general synthetic procedures A or B.

General Procedure A

A solution of a primary or secondary amine (10 mmol, 1 equiv), 1-methyl-3-oxocyclobutane-1-carboxylic acid (1.66 g, 13 mmol, 1.3 equiv), and a reducing agent (13 mmol, 1.3 equiv) in toluene (0.2 M) are heated to reflux with a Dean-Stark setup. After residual water appears in the trap, the reaction is cooled to ambient temperature. Work up can then be done following one of the following protocols: (1) First toluene is removed in vacuo and the residue is partitioned between water (30 mL) and methyl t-butyl ether (50 mL). The aqueous layer is washed with methyl t-butyl ether two more times (50 mL each). After removal of water in a high vac, the ratio of cis/trans isomers is determined by HPLC. (2) The toluene is replaced with ethyl acetate and heptane is added to obtain a solid material, which is filtered, dried in a vacuum, and the ratio of cis/trans diastereomers is determined by HPLC.

The method used to determine the cis/trans diastereomer ratio can be: (a) XBridge C18 3.5 mM 4.6×150 mm HPLC column, 1 mL/min flow rate, 0 to 100% water (+0.1% ammonia)/acetonitrile(+0.1% ammonia) over 30 min; or (b) $^1$H NMR.

General Procedure B

A solution of a primary or secondary amine (1 equiv), g-ketocarboxylic acid (1.0-1.3 equiv), and a Hantzsch ester (1.0-1.3 equiv) in toluene (0.2 M) is heated to reflux with a Dean-Stark setup. After residual water appears in the trap, the reaction is cooled to ambient temperature. Toluene is removed in vacuo and the residue was partitioned between water and methyl t-butyl ether. If needed, 5 equiv of 3M aqueous NaOH is added. The aqueous layer is then washed with methyl t-butyl ether two more times and then, if NaOH is used, the pH is brought to neutral by addition of 3M HCl solution. The product is extracted with dichloromethane and the ratio of cis/trans diastereomers is determined by HPLC or NMR.

Examples 1-5. Reductive amination using general procedure A in preparation of trans-3-((R)-3-(1-(tert-butoxycarbonyl)azetidin-3-yl)piperidin-1-yl)-1-methylcyclobutane-1-carboxylic acid

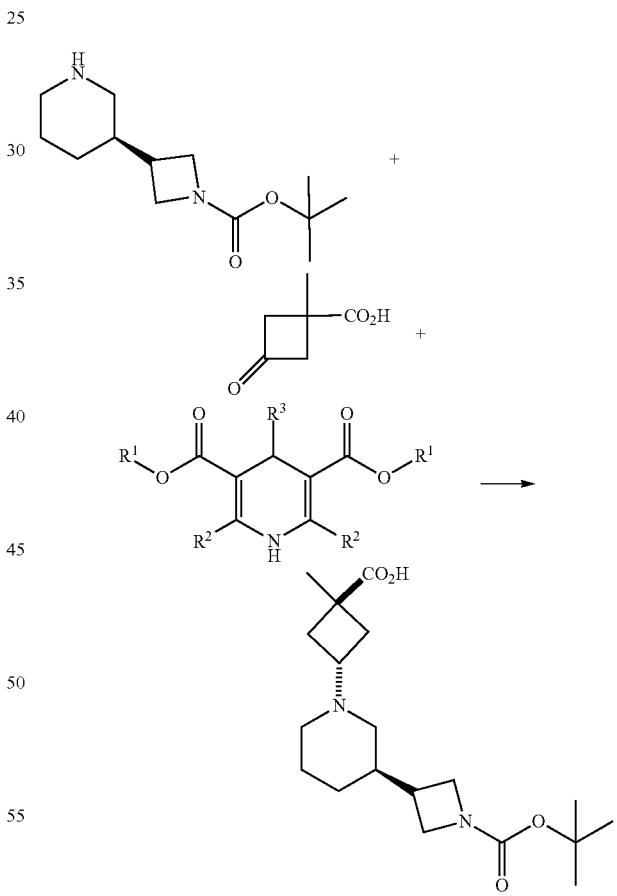

A solution of tert-butyl 3-[(3R)-3-piperidyl]azetidine-1-carboxylate (23.2 g, 96.5 mmol), 1-methyl-3-oxocyclobutane-1-carboxylic acid (16.1 g, 125.5 mmol, 1.3 equiv), and a reducing agent (see Table A) (in toluene (480 mL, 0.2 M) was heated to reflux with a Dean-Stark trap and condenser attached. After water appeared in the trap, the reaction was cooled to ambient temperature. Toluene was removed in vacuo and the residue was partitioned between water (300 mL) and methyl t-butyl ether (500 mL). The aqueous layer was then washed with methyl t-butyl ether two more times (500 mL each). After removal of water in a high vac, the ratio of cis/trans diastereomers was 3:97 as determined by HPLC. The trans diastereomer was retained at 9.1 min, and the cis diastereomer was retained at 10.1 min.

$^1$H NMR (400 MHz, CDCl3) trans diastereomer: 3.82 (q, J=8.0 Hz, 2H), 3.60 (dt, J=28.6, 7.6 Hz, 2H), 3.24-2.97 (m, 3H), 2.51 (s, 2H), 2.15 (d, J=8.6 Hz, 3H), 2.08-1.86 (m, 2H), 1.84-1.57 (m, 4H), 1.31 (s, 9H), 1.25 (s, 3H), 0.92-0.70 (m, 1H) ppm.

$^{13}$C NMR (400 MHz, CDCl3) trans diastereomer: 181.25, 156.14, 79.32, 55.75, 51.95, 51.93, 49.40, 38.28, 37.16, 36.15, 31.94, 28.31, 26.03, 25.94, 22.18 ppm.

LCMS [M+H]: 353.1.

| Example | Reducing Agent | $R^1$ | $R^2$ | $R^3$ | Moles | Equiv | Trans/Cis | Yield |
|---|---|---|---|---|---|---|---|---|
| 1 | diethyl 2,6-dimethyl-1,4-dihydropyridine-3,5-dicarboxylate | Et | Me | H | 125.5 mmol | 1.3 | 97.5:2.5 | 94% |
| 2 | dimethyl 2,6-dimethyl-1,4-dihydropyridine-3,5-dicarboxylate | Me | Me | H | 125.5 mmol | 1.3 | 98.0:2.0 | 94% |
| 3 | diethyl 2,6-diethyl-1,4-dihydropyridine-3,5-dicarboxylate | Et | Et | H | 125.5 mmol | 1.3 | 97.0:3.0 | 95% |
| 4 | diethyl 2,4,6-trimethyl-1,4-dihydropyridine-3,5-dicarboxylate | Et | Me | Me | 125.5 mmol | 1.3 | 97.5:2.5 | 52% |
| 5 | di-tert-butyl 2,6-dimethyl-1,4-dihydropyridine-3,5-dicarboxylate | t-Bu | Me | H | 125.5 mmol | 1.3 | 98.5:1.5 | 99% |

Example 6. Reductive amination using general procedure B in preparation of trans-3-((R)-3-(1-(tert-butoxycarbonyl)azetidin-3-yl)piperidin-1-yl)-1-methylcyclopentane-1-carboxylic acid (Mixture of Diastereomers)

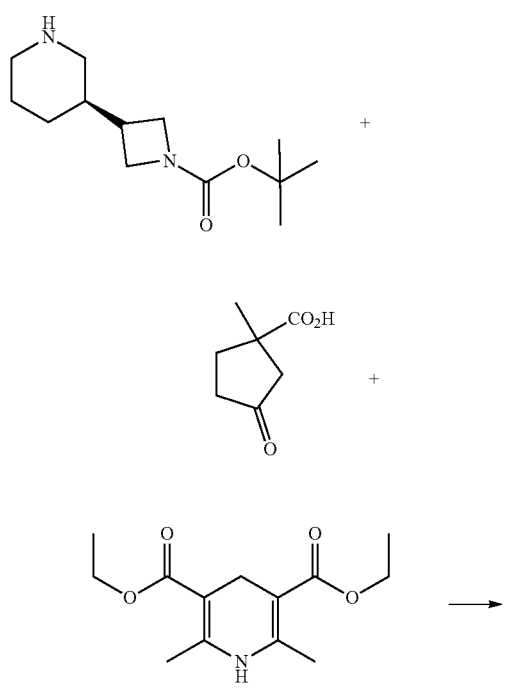

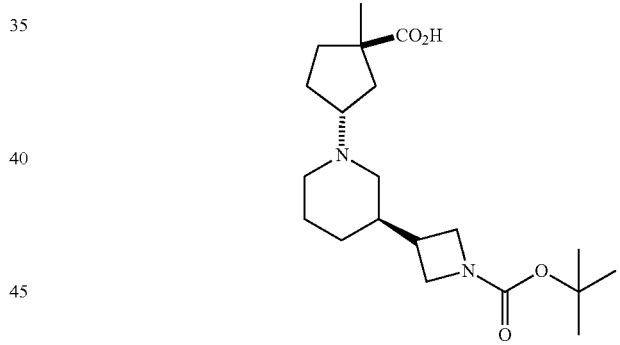

To a 25-mL round bottom flask was added 1-methyl-3-oxo-cyclopentanecarboxylic acid (231 mg, 1.62 mmol), tert-butyl 3-[(3R)-3-piperidyl]azetidine-1-carboxylate (300 mg, 1.25 mmol), and 6 mL of toluene. Diethyl 2,6-dimethyl-1,4-dihydropyridine-3,5-dicarboxylate (411 mg, 1.62 mmol) was added to the solution, the flask was equipped with a Dean-Stark setup, and then the mixture was heated to reflux. The reflux was continued for 3 h and then the reaction was cooled to ambient temperature. The reaction mixture was concentrated in vacuo to remove toluene and the residue was partitioned between water and methyl tert-butyl ether. The separated phases were then washed with methyl tert-butyl ether (4×5 mL). The aqueous phase was then concentrated in vacuo to afford 362 mg (79% yield) of trans-3-((R)-3-(1-(tert-butoxycarbonyl) azetidin-3-yl)piperidin-1-yl)-1-methylcyclopentane-1-carboxylic acid as a mixture of diastereomers. The cis/trans diastereomer ratio was determined by $^1$H NMR to be less than 1:20 (i.e., more than 20-fold greater amount of trans diastereomer than cis diastereomer).

¹H NMR (400 MHz, Methanol-d4) mixture of trans isomers: δ 4.07-3.90 (m, 2H), 3.83-3.65 (m, 2H), 3.65-3.47 (m, 2H), 3.45-3.31 (m, 1H), 2.87-2.65 (m, 1H), 2.55-2.34 (m, 3H), 2.26-2.12 (m, 1H), 2.12-1.91 (m, 4H), 1.91-1.70 (m, 3H), 1.61 (ddd, J=13.2, 7.5, 5.5 Hz, 1H), 1.43 (s, 9H), 1.27 (s, 3H), 1.23-1.06 (m, 1H).

LCMS [M+H]: 367.2.

Example 7. Reductive amination using general procedure B in preparation of trans-3-(dibenzylamino)-1-methylcyclopentane-1-carboxylic acid (Mixture of Enantiomers)

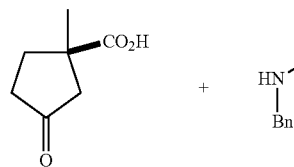
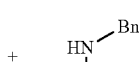

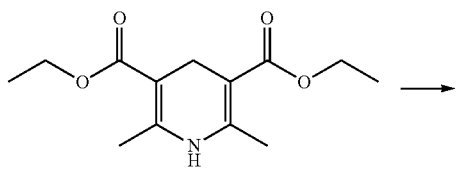

1-Methyl-3-oxo-cyclopentanecarboxylic acid (72 mg, 0.51 mmol, 1 equiv), dibenzylamine (100 mg, 0.51 mmol, 1 equiv), and the Hantzsch ester (141 mg, 0.56 mmol, 1.1 equiv) were dissolved in 3 mL of toluene (0.17M). The reaction mixture was refluxed with a Dean-Stark setup for 2 hours and then brought to ambient temperature. Toluene was removed in vacuo and the residue was partitioned between water (5 mL) with 5 equiv of 3M NaOH and methyl tert-butyl ether (5 mL). The aqueous layer was washed with two additional portions of methyl tert-butyl ether (5 mL each) and then neutralized to pH 7 with 3M HCl. Then the aqueous layer was extracted with dichloromethane, the organic layer was dried with MgSO₄, filtered through celite and concentrated in vacuo. The yield of the crude trans-3-(dibenzylamino)-1-methylcyclopentane-1-carboxylic acid (mixture of two trans enantiomers) was 100 mg (61%) and the cis/trans ratio of enantiomers was 1:9 as determined by ¹H NMR.

¹H NMR (400 MHz, Methanol-d4) mixture of trans isomers: d 7.36-7.21 (m, 10H), 3.93 (s, 0.2H), 3.74 (s, 3.8H), 3.62-3.53 (m, 0.1H), 3.52-3.40 (m, 0.9H), 2.52-2.38 (m, 1H), 2.17-2.06 (1H), 2.03-1.70 (m, 2H), 1.59-1.44 (m, 2H), 1.30 (s, 2.7H), 1.21 (s, 0.3H) ppm.

LCMS [M+H]: 324.1.

Example 8. Reductive amination using general procedure A in preparation of trans-4-((R)-3-(1-(tert-butoxycarbonyl)azetidin-3-yl)piperidin-1-yl)-1-methylcyclohexane-1-carboxylic acid

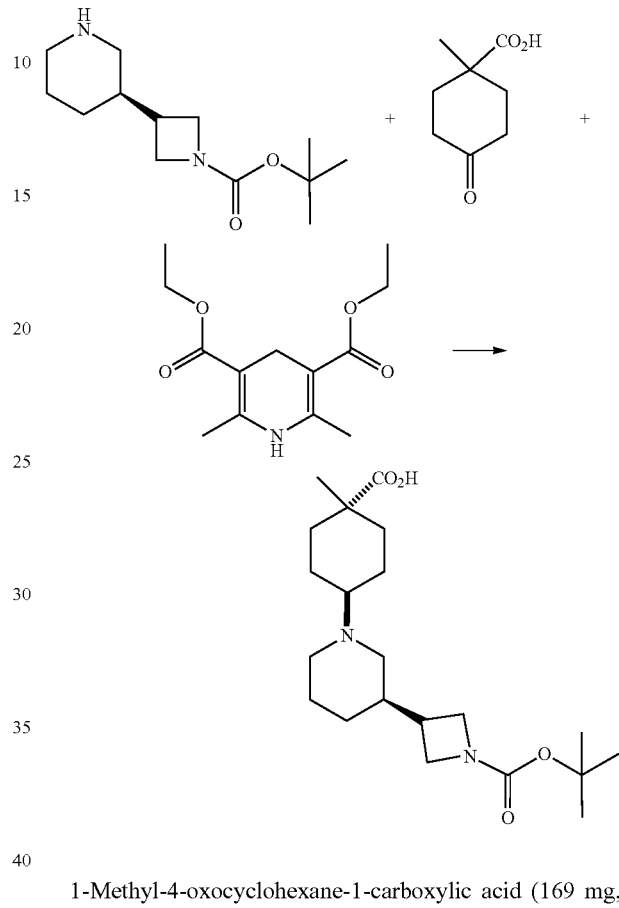

1-Methyl-4-oxocyclohexane-1-carboxylic acid (169 mg, 1.08 mmol, 1.3 equiv) was mixed with tert-butyl 3-[(3R)-3-piperidyl]azetidine-1-carboxylate (200 mg, 0.83 mmol, 1 equiv) and the Hantzsch ester (274 mg, 1.08 mmol, 1.3 equiv) in 4.5 mL of toluene and the mixture was refluxed with a Dean-Stark setup for 3 hrs under an inert atmosphere. Then toluene was removed in vacuo and the residue was partitioned between water (10 mL) and methyl tert-butyl ether (10 mL) with an addition of 3M NaOH (5 equiv). The aqueous layer was washed with methyl tert-butyl ether two more times and then neutralized with 3M HCl to pH 7. The mixture was extracted with dichloromethane, dried with MgSO₄, filtered through celite, and concentrated in vacuo. The yield of trans-4-((R)-3-(1-(tert-butoxycarbonyl)azetidin-3-yl)piperidin-1-yl)-1-methylcyclohexane-1-carboxylic acid was 75% (236 mg), and the cis/trans diastereomer ratio was determined by ¹H NMR to be less than 1:20 (i.e., more than 20-fold greater amount of trans diastereomer than cis diastereomer).

¹H NMR (400 MHz, Methanol-d₄) δ 4.03-3.94 (m, 2H), 3.81-3.65 (m, 2H), 3.44 (d, J=12.0 Hz, 1H), 3.29 (d, J=9.6 Hz, 1H), 3.07-2.98 (m, 1H), 2.83 (td, J=12.2, 3.1 Hz, 1H), 2.55 (t, J=11.8 Hz, 1H), 2.45-2.27 (m, 1H), 2.09-1.62 (m, 12H), 1.43 (s, 9H), 1.19 (s, 3H), 1.12-1.03 (m, 1H) ppm.

LCMS [M+H]: 381.0.

Example 9. Reductive amination using general procedure A in preparation of trans-4-(4-(4-methoxyphenyl)piperidin-1-yl)-1-methylcyclohexane-1-carboxylic acid

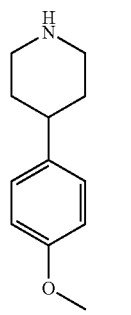 + 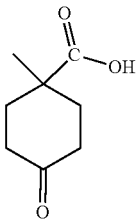 +

General Synthetic Procedures for Synthesis of CCR4 Antagonists:

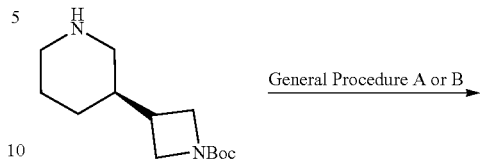

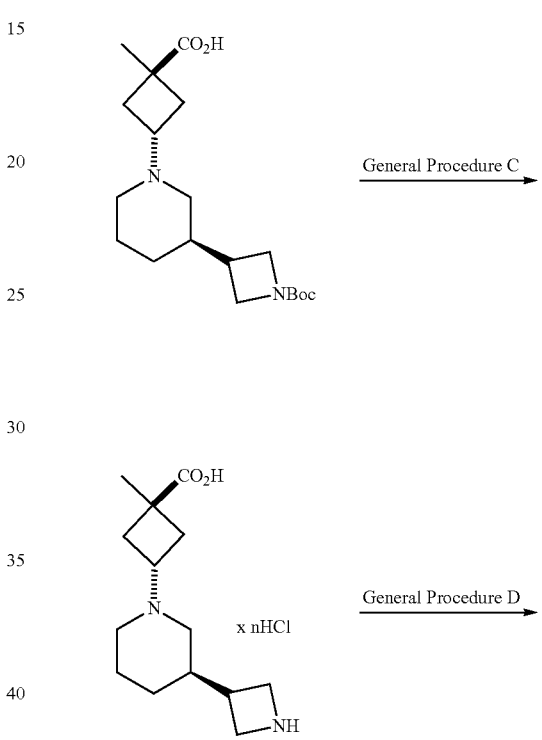

CCR4 Antagonist Compounds

1-Methyl-4-oxocyclohexane-1-carboxylic acid (169 mg, 1.08 mmol, 1.3 equiv) was mixed with tert-butyl 4-(4-methoxyphenyl)piperidine (159 mg, 0.83 mmol, 1 equiv) and the Hantzsch ester (274 mg, 1.08 mmol, 1.3 equiv) in 4.5 mL of toluene and the mixture was refluxed with a Dean-Stark setup for 3 hrs under inert atmosphere. Then toluene was removed in vacuo and the residue was partitioned between water (10 mL) and methyl tert-butyl ether (10 mL) with an addition of 3M NaOH (5 equiv). The aqueous layer was washed with methyl tert-butyl ether two more times and then neutralized with 3M HCl to pH 7. The mixture was extracted with dichloromethane, dried with $MgSO_4$, filtered through celite, and concentrated in vacuo. The yield of trans-4-(4-(4-methoxyphenyl)piperidin-1-yl)-1-methylcyclohexane-1-carboxylic acid was 63% (173 mg), and the cis/trans isomer ratio was determined by $^1$H NMR to be less than 1:20 (i.e., more than 20-fold greater amount of trans isomer than cis isomer).

$^1$H NMR (400 MHz, Methanol-$d_4$) δ 7.20-7.13 (m, 2H), 6.90-6.85 (m, 2H), 3.77 (s, 3H), 3.62-3.55 (m, 2H), 3.16-3.07 (m, 3H), 2.81 (tt, J=12.0, 4.0 Hz, 1H), 2.11-1.66 (m, 12H), 1.22 (s, 3H) ppm.

LCMS [M+H]: 332.0.

General Procedure C

Trans-3-((R)-3-(1-(tert-butoxycarbonyl)azetidin-3-yl)piperidin-1-yl)-1-methylcyclobutane-1-carboxylic acid is dissolved in water (telescoped aqueous solution from general procedure A may also be used for this step) and 5 equivalents of concentrated HCl is added to the solution and the mixture is stirred at room temperature until complete conversion is observed by LC-MS. The solution is neutralized with 6N NaOH to pH 7 and used in the next step.

Alternatively, to trans-3-((R)-3-(1-(tert-butoxycarbonyl)azetidin-3-yl)piperidin-1-yl)-1-methylcyclobutane-1-carboxylic acid, 5 equivalents of 1N HCl in ethyl acetate is added at ambient temperature and the solution is stirred until full conversion is reached and solid deprotected product precipitated. Solid trans-3-((R)-3-(azetidin-3-yl)piperidin-1-yl)-1-methylcyclobutane-1-carboxylic acid hydrochloride salt is filtered and dried in high vacuum. In addition to HCl, other strong acids can be used in General Procedure C, such as sulfuric acid, mesic acid, tosic acid, bezic acid, phosphoric acid, HBr, HI, etc. In addition to ethyl acetate, other organic solvents can be used in General Procedure C for deprotection.

General Procedure D

An electrophilic intermediate compound is first selected (i.e., one of intermediate compounds in Table 1 for the synthesis of the CCR4 antagonists of Examples 10-19); 1 eq) and mixed with trans-3-((R)-3-(azetidin-3-yl)piperidin-1-yl)-1-methylcyclobutane-1-carboxylic acid (1.2-1.5 eq) by dissolving in equal volumes of water and tert-butanol to make up 0.2-0.5 M biphasic solution. 6 Equivalents of sodium hydroxide (as 50% wt aqueous solution) is added to that solution and the reaction mixture is heated to 80° C. until full conversion is observed by LC-MS. Then, the reaction mixture is cooled to ambient temperature and the layers are separated. The aqueous layer is washed with fresh tert-butanol and organic fractions are combined. Tert-butanol is removed under reduced pressure to obtain the desired CCR4 antagonist compound. In addition to tert-butanol, other organic solvents can be used in General Procedure D such as methanol, ethanol, isopropanol, butanol, dioxanes, THF, meTHF, DMSO, and others. In addition to NaOH, other bases can be used in General Procedure D such as KOH, LiOH, $Ba(OH)_2$, $Ca(OH)_2$, amines, phosphates, carbonates, and others.

Examples 10-19

Syntheses of the following CCR4 antagonists were carried out following General Procedures A, C and D wherein General Procedure D was used with the intermediates shown in Table 1 to produce the final CCR4 antagonist compounds shown in Table 1. In these intermediates X is F, Cl, Br, I, or —$OS(O)_2R$; and R is alkyl, perfluoroalkyl or aryl.

TABLE 1

| Example | General Procedure D Intermediate | CCR4 Antagonist |
|---|---|---|
| 10 | 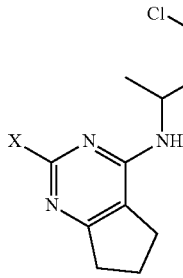 | 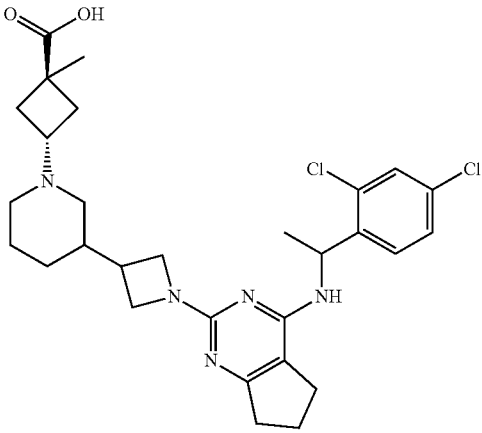 [SMILES: CC(Nc1nc(N2CC(C3CCCN([C@H]4C[C@](C)(C(=O)O)C4)C3)C2)nc2c1CCC2)c1ccc(Cl)cc1Cl] |
| 11 | 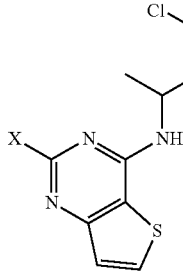 | 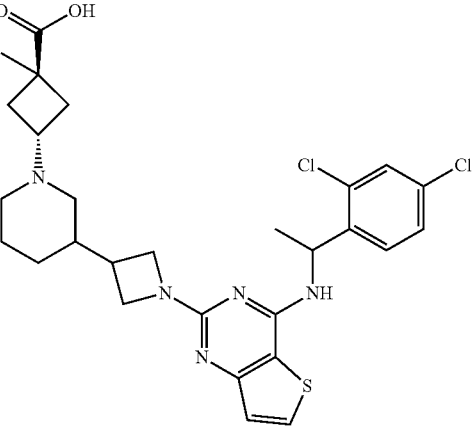 |

TABLE 1-continued

| Example | General Procedure D Intermediate | CCR4 Antagonist |
|---|---|---|
| 12 | | |
| 13 | | |
| 14 | | |

TABLE 1-continued
| Example | General Procedure D Intermediate | CCR4 Antagonist |
|---|---|---|
| 15 | 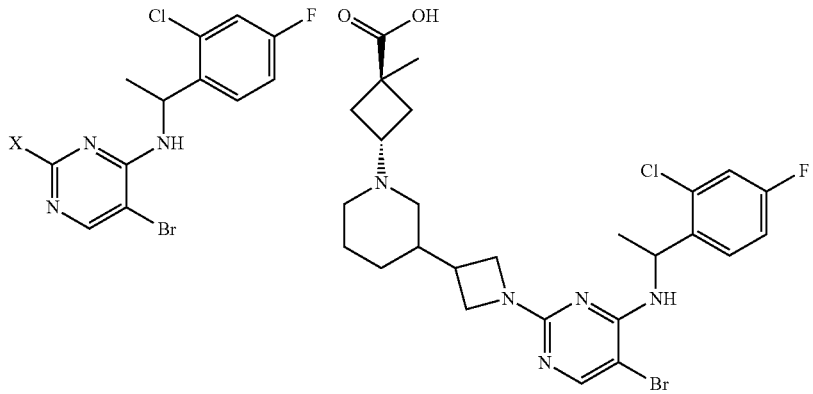 | 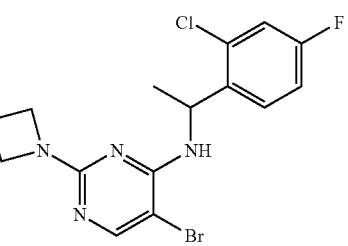 |
| 16 | 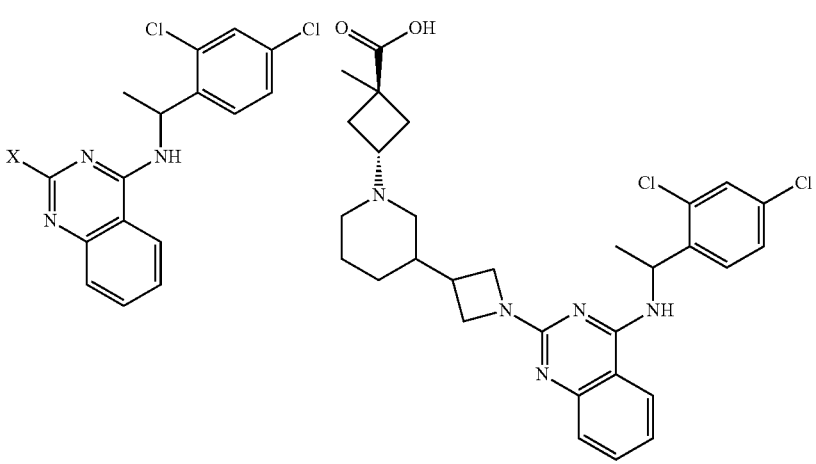 | 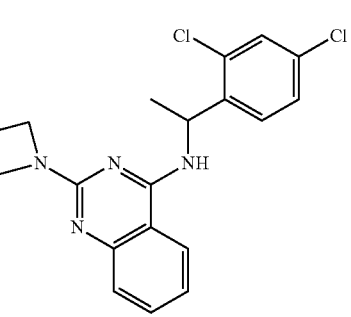 |
| 17 | 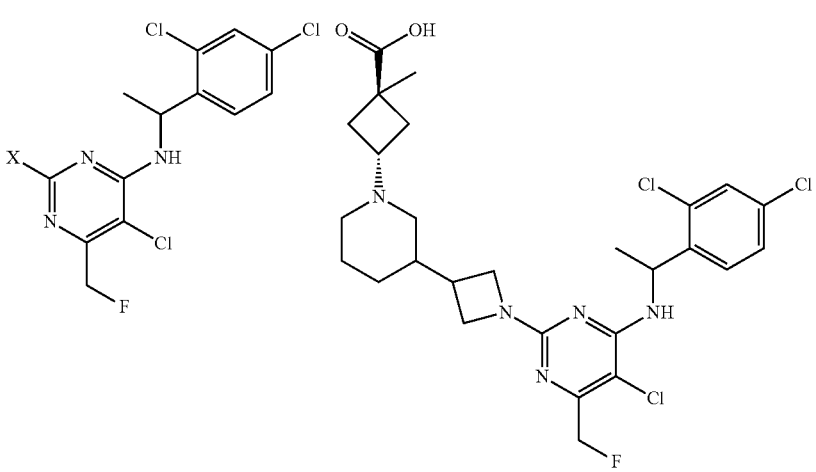 | 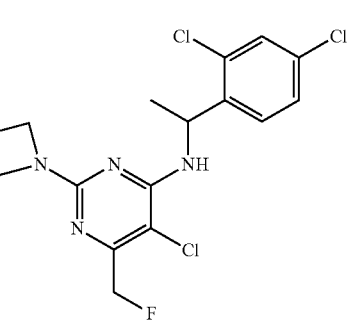 |

TABLE 1-continued

| Example | General Procedure D Intermediate | CCR4 Antagonist |
|---|---|---|
| 18 | 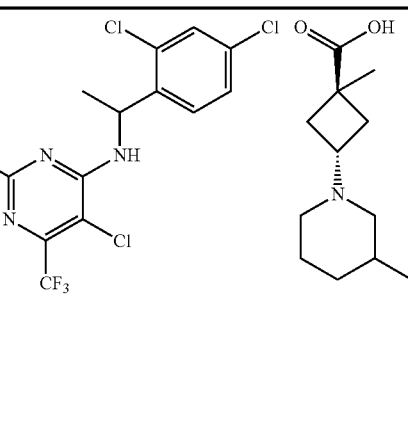 | 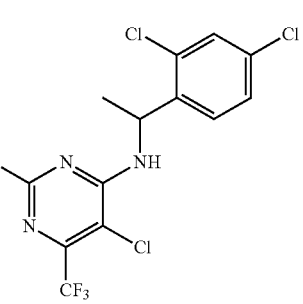 |
| 19 | 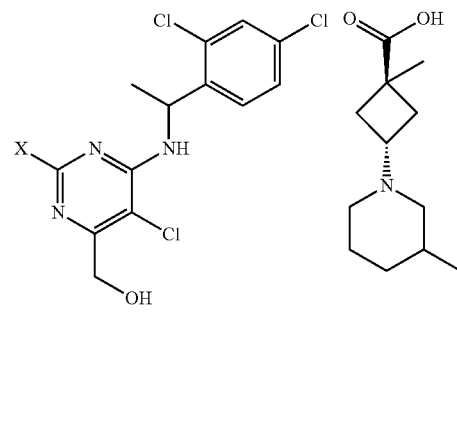 | 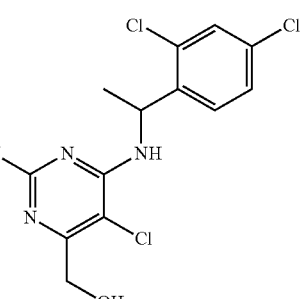 |

Example 20

Synthesis of a precursor of a CCR4 antagonist, trans-3-((R)-3-(1-(tert-butoxycarbonyl) azetidin-3-yl) piperidin-1-yl)-1-methylcyclobutane-1-carboxylic acid, is carried out as follows. A solution of tert-butyl 3-[(3R)-3-piperidyl]azetidine-1-carboxylate (55.6 mol) in toluene (69 L, 0.80 M) added to a reactor containing 1-methyl-3-oxocyclobutane-1-carboxylic acid (9.27 kg, 72.3 mol, 1.3 equiv) and the Hantzsch ester diethyl 2,6-dimethyl-1,4-dihydropyridine-3,5-dicarboxylate (18.3 kg, 72.3 mmol, 1.3 equiv). Toluene (170 L) is charged, a Dean-Stark trap is attached and the reaction mixture is heated to 100-110° C. for ≥3 h. Reaction volume is reduced in vacuo (to 115 L total), nBuOAc (230 L) is added, and the mixture is concentrated again (to 200-230 L total). This cycle is repeated twice more before heptane (135 L) is added. The resulting solid is collected by filtration, washed with a 1:1 mixture of EtOAc/heptane (~60 L), and dried under vacuum to obtain trans-3-((R)-3-(1-(tert-butoxycarbonyl)azetidin-3-yl)piperidin-1-yl)-1-methylcyclobutane-1-carboxylic acid as a white solid (16.7 kg, 47.4 mol, 85% yield, >99% trans by HPLC).

In view of the foregoing detailed description of preferred embodiments of the present disclosure, it readily will be understood by those persons skilled in the art that the present disclosure is susceptible to broad utility and application. While various aspects have been described in the context of screen shots, additional aspects, features, and methodologies of the present disclosure will be readily discernable therefrom. Many embodiments and adaptations of the present disclosure other than those herein described, as well as many variations, modifications, and equivalent arrangements and methodologies, will be apparent from or reasonably suggested by the present disclosure and the foregoing description thereof, without departing from the substance or scope of the present disclosure. Furthermore, any sequence(s) and/or temporal order of steps of various processes described and claimed herein are those considered to be the best mode contemplated for carrying out the present disclosure. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present invention. In addition, some steps may be carried out simultaneously. Accordingly, while the present disclosure has been described herein in detail in relation to preferred embodiments, it is to be understood that this disclosure is only illustrative and exemplary of the present disclosure and is made merely for purposes of providing a full and enabling disclosure of the disclosure. The foregoing disclosure is not intended nor is to be construed to limit the present disclosure or otherwise to exclude any such other embodiments, adaptations, variations, modifications and equivalent arrangements, the present disclosure being limited only by the claims appended hereto and the equivalents thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Embodiments

Embodiment 1. A method of synthesis of a compound of formula (III), said method comprising reacting a compound of formula (I) with a compound of formula (II) in the presence of a carboxylic acid directed reducing agent to form the compound of formula (III):

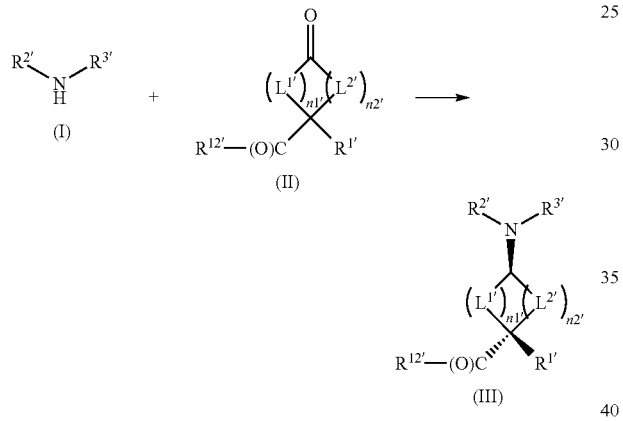

wherein
n1' and n2' are each independently an integer from 0 to 5, wherein the sum of n1' and n2' is at least 1 and not more than 6;
$L^{1'}$ is $C(R^{4'})_2$;
$L^{2'}$ is $C(R^{5'})_2$;
$R^{1'}$ is hydrogen, halogen, $-CX^{1'}_3$, $-CHX^{1'}_2$, $-CH_2X^{1'}$, $-OCX^{1'}_3$, $-OCHX^{1'}_2$, $-OCH_2X^{1'}$, $-CN$, $-S(O)_2R^{1'A}$, $-SR^{1'A}$, $-S(O)R^{1'A}$, $-SO_2NR^{1'A}R^{1'B}$, $-NHC(O)NR^{1'A}R^{1'B}$, $-N(O)_2$, $-NR^{1'A}R^{1'B}$, $-NHNR^{1'A}R^{1'B}$, $-C(O)R^{1'A}$, $-C(O)-OR^{1'A}$, $-C(O)NR^{1'A}R^{1'B}$, $-C(O)NHNR^{1'A}R^{1'B}$, $-OR^{1'A}$, $-NR^{1'A}SO_2R^{1'B}$, $-NR^{1'A}C(O)R^{1'B}$, $-NR^{1'A}C(O)OR^{1'B}$, $-NR^{1'A}OR^{1'B}$, $-N_3$, substituted or unsubstituted alkyl, substituted or unsubstituted heteroalkyl, substituted or unsubstituted cycloalkyl, substituted or unsubstituted heterocycloalkyl; substituted or unsubstituted aryl, or substituted or unsubstituted heteroaryl;
$R^{2'}$ is hydrogen, $-CX^{2'}_3$, $-CHX^{2'}_2$, $-CH_2X^{2'}$, $-OCX^{2'}_3$, $-OCHX^{2'}_2$, $-OCH_2X^{2'}$, $-SR^{2'A}$, $-NR^{2'A}R^{2'B}$, $-NHNR^{2'A}R^{2'B}$, $-OR^{2'A}$, $-NR^{2'A}SO_2R^{2'B}$, $-NR^{2'A}C(O)R^{2'B}$, $-NR^{2'A}C(O)OR^{2'B}$, $-NR^{2'A}OR^{2'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl;
$R^{3'}$ is halogen, $-CX^{3'}_3$, $-CHX^{3'}_2$, $-CH_2X^{3'}$, $-OCX^{3'}_3$, $-OCHX^{3'}_2$, $-OCH_2X^{3'}$, $-SR^{3'A}$, $-NR^{3'A}R^{3'B}$, $-NHNR^{3'A}R^{3'B}$, $-OR^{3'A}$, $-NR^{3'A}SO_2R^{3'B}$, $-NR^{3'A}C(O)R^{3'B}$, $-NR^{3'A}C(O)OR^{3'B}$, $-NR^{3'A}OR^{3'B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{2'}$ and $R^{3'}$ may optionally be joined to form a substituted or unsubstituted heterocycloalkyl;
$R^{4'}$ is independently hydrogen, halogen, $-CX^{4'}_3$, $-CHX^{4'}_2$, $-CH_2X^{4'}$, $-OCX^{4'}_3$, $-OCHX^{4'}_2$, $-OCH_2X^{4'}$, $-CN$, $-S(O)_2R^{4'A}$, $-SR^{4'A}$, $-S(O)R^{4'A}$, $-SO_2NR^{4'A}R^{4'B}$, $-NHC(O)NR^{4'A}R^{4'B}$, $-N(O)_2$, $-NR^{4'A}R^{4'B}$, $-NHNR^{4'A}R^{4'B}$, $-C(O)R^{4'A}$, $-C(O)-OR^{4'A}$, $-C(O)NR^{4'A}R^{4'B}$, $-C(O)NHNR^{4'A}R^{4'B}$, $-OR^{4'A}$, $-NR^{4'A}SO_2R^{4'B}$, $-NR^{4'A}C(O)R^{4'B}$, $-NR^{4'A}C(O)OR^{4'B}$, $-NR^{4'A}OR^{4'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{5'}$ is independently hydrogen, halogen, $-CX^{5'}_3$, $-CHX^{5'}_2$, $-CH_2X^{5'}$, $-OCX^{5'}_3$, $-OCHX^{5'}_2$, $-OCH_2X^{5'}$, $-CN$, $-S(O)_2R^{5'A}$, $-SR^{5'A}$, $-S(O)R^{5'A}$, $-SO_2NR^{5'A}R^{5'B}$, $-NHC(O)NR^{5'A}R^{5'B}$, $-N(O)_2$, $-NR^{5'A}R^{5'B}$, $-NHNR^{5'A}R^{5'B}$, $-C(O)R^{5'A}$, $-C(O)-OR^{5'A}$, $-C(O)NR^{5'A}R^{5'B}$, $-C(O)NHNR^{5'A}R^{5'B}$, $-OR^{5'A}$, $-NR^{5'A}SO_2R^{5'B}$, $-NR^{5'A}C(O)R^{5'B}$, $-NR^{5'A}C(O)OR^{5'B}$, $-NR^{5'A}OR^{5'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{12'}$ is independently $-OH$ or $NHR^{12''}$;
$R^{12''}$ is hydrogen or a substituted or unsubstituted alkyl;
$R^{1'A}$, $R^{1'B}$, $R^{2'A}$, $R^{2'B}$, $R^{3'A}$, $R^{3'B}$, $R^{4'A}$, $R^{4'B}$, $R^{5'A}$, and $R^{5'B}$ are independently hydrogen, $-F$, $-Cl$, $-Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-C(O)OH$, $-C(O)NH_2$, $-OH$, $-NH_2$, $-COOH$, $-CONH_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2'A}$ and $R^{2'B}$ substituents bonded to the same nitrogen atom may optionally be joined to form a substituted or unsubstituted heterocycloalkyl or substituted or unsubstituted heteroaryl; or $R^{3'A}$ and $R^{3'B}$ substituents bonded to the same nitrogen atom may optionally be joined to form a substituted or unsubstituted heterocycloalkyl or substituted or unsubstituted heteroaryl; and
$X^{1'}$, $X^{2'}$, $X^{3'}$, $X^{4'}$, and $X^{5'}$ are independently halogen.

Embodiment 2. The method of embodiment 1, wherein the method is used to make an antagonist of C—C chemokine receptor type 4 (CCR4), or a salt or ester thereof.

Embodiment 3. The method of embodiment 1 or 2, wherein the compound of formula (III) is in at least 80% trans isomerically pure form.

Embodiment 4. The method of any one of embodiments 1 to 3, wherein the carboxylic acid directed reducing agent is a 1,4-dihydropyridine.

Embodiment 5. The method of any one of embodiments 1 to 4, wherein the carboxylic acid directed reducing agent is the 1,4-dihydropyridine of formula (IV):

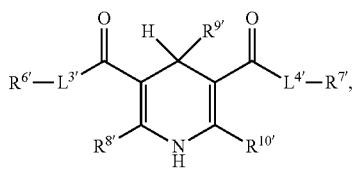

wherein:

$L^{3'}$ and $L^{4'}$ are independently O or $NR^{20'}$;

$R^{20'}$ is independently hydrogen or $R^{21'}$;

$R^{21'}$ is independently hydrogen, $-CX^{21'}_3$, $-CHX^{21'}_2$, $-CH_2X^{21'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl $R^{6'}$ is independently hydrogen, $-CX^{6'}_3$, $-CHX^{6'}_2$, $-CH_2X^{6'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or a bond attaching the 1,4-dihydropyridine to a polymer support;

$R^{7'}$ is independently hydrogen, $-CX^{7'}_3$, $-CHX^{7'}_2$, $-CH_2X^{7'}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bond attaching the 1,4-dihydropyridine to a polymer support;

$R^{8'}$ is independently hydrogen, halogen, $-CX^{8'}_3$, $-CHX^{8'}_2$, $-CH_2X^{8'}$, $-OCX^{8'}_3$, $-OCHX^{8'}_2$, $-OCH_2X^{8'}$, $-CN$, $-S(O)_2R^{8'A}$, $-SR^{8'A}$, $-S(O)R^{8'A}$, $-SO_2NR^{8'A}R^{8'B}$, $-NHC(O)NR^{8'A}R^{8'B}$, $-N(O)_2$, $-NR^{8'A}R^{8'B}$, $-NHNR^{8'A}R^{8'B}$, $-C(O)R^{8'A}$, $-C(O)-OR^{8'A}$, $-C(O)NR^{8'A}R^{8'B}$, $-C(O)NHNR^{8'A}R^{8'B}$, $-OR^{8'A}$, $-NR^{8'A}SO_2R^{8'B}$, $-NR^{8'A}C(O)R^{8'B}$, $-NR^{8'A}C(O)OR^{8'B}$, $-NR^{8'A}OR^{8'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{9'}$ is independently hydrogen, halogen, $-CX^{9'}_3$, $-CHX^{9'}_2$, $-CH_2X^{9'}$, $-OCX^{9'}_3$, $-OCHX^{9'}_2$, $-OCH_2X^{9'}$, $-CN$, $-S(O)_2R^{9'A}$, $-SR^{9'A}$, $-S(O)R^{9'A}$, $-SO_2NR^{9'A}R^{9'B}$, $-NHC(O)NR^{9'A}R^{9'B}$, $-N(O)_2$, $-NR^{9'A}R^{9'B}$, $-NHNR^{9'A}R^{9'B}$, $-C(O)R^{9'A}$, $-C(O)-OR^{9'A}$, $-C(O)NR^{9'A}R^{9'B}$, $-C(O)NHNR^{9'A}R^{9'B}$, $-OR^{9'A}$, $-NR^{9'A}SO_2R^{9'B}$, $-NR^{9'A}C(O)R^{9'B}$, $-NR^{9'A}C(O)OR^{9'B}$, $-NR^{9'A}OR^{9'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10'}$ is independently hydrogen, halogen, $-CX^{10'}_3$, $-CHX^{10'}_2$, $-CH_2X^{10'}$, $-OCX^{10'}_3$, $-OCHX^{10'}_2$, $-OCH_2X^{10'}$, $-CN$, $-S(O)_2R^{10'A}$, $-SR^{10'A}$, $-S(O)R^{10'A}$, $-SO_2NR^{10'A}R^{10'B}$, $-NHC(O)NR^{10'A}R^{10'B}$, $-N(O)_2$, $-NR^{10'A}R^{10'B}$, $-NHNR^{10'A}R^{10'B}$, $-C(O)R^{10'A}$, $-C(O)-OR^{10'A}$, $-C(O)NR^{10'A}R^{10'B}$, $-C(O)NHNR^{10'A}R^{10'B}$, $-OR^{10'A}$, $-NR^{10'A}SO_2R^{10'B}$, $-NR^{10'A}C(O)R^{10'B}$, $-NR^{10'A}C(O)OR^{10'B}$, $-NR^{10'A}OR^{10'B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8'A}$, $R^{8'B}$, $R^{9'A}$, $R^{9'B}$, $R^{10'A}$ and $R^{10'B}$ are independently hydrogen, $-F$, $-Cl$, $-Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-C(O)OH$, $-C(O)NH_2$, $-OH$, $-NH_2$, $-COOH$, $-CONH_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^{6'}$, $X^{7'}$, $X^{8'}$, $X^{9'}$, $X^{10'}$ and $X^{21'}$ are independently halogen.

Embodiment 6. The method of any one of embodiments 1 to 5, wherein $L^{3'}$ and $L^{4'}$ are both O.

Embodiment 7. The method of any one of embodiments 1 to 5, wherein $R^{6'}$ and $R^{7'}$ are independently a substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a bond attaching the 1,4-dihydropyridine to a polymer support.

Embodiment 8. The method of any one of embodiments 1 to 5, wherein $R^{8'}$, $R^{9'}$ and $R^{10'}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 9. The method of any one of embodiments 1 to 8, wherein n1' and n2' are independently 1 or 2 and $R^{1'}$ is a substituted or unsubstituted $C_1$-$C_4$ alkyl.

Embodiment 10. The method of any one of embodiments 1 to 9, wherein n1' and n2' are independently 1 and $L^{1'}$ and $L^{2'}$ are independently substituted or unsubstituted $C_1$-$C_2$ alkyl.

Embodiment 11. The method of any one of embodiments 1 to 10, wherein $R^{2'}$ and $R^{3'}$ are joined to form a substituted or unsubstituted piperidinyl.

Embodiment 12. The method of any one of embodiments 1 to 11, wherein the piperidinyl is substituted with a substituted or unsubstituted heterocycloalkyl.

Embodiment 13. The method of any one of embodiments 1 to 12, wherein the substituted or unsubstituted heterocycloalkyl is nitrogen-containing 3 membered to 6-membered heterocycloalkyl.

Embodiment 14. The method of embodiment 1, wherein the compound of formula (I) is:

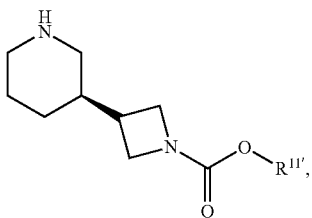

wherein:

$R^{11'}$ is independently —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 15. The method of embodiment 14, wherein $R^{11'}$ is a substituted or unsubstituted alkyl.

Embodiment 16. The method of embodiment 14 or 15, wherein $R^{11'}$ is a substituted or unsubstituted C$_1$-C$_4$ alkyl.

Embodiment 17. The method of any one of embodiments 14 to 16, wherein the compound of formula III is:

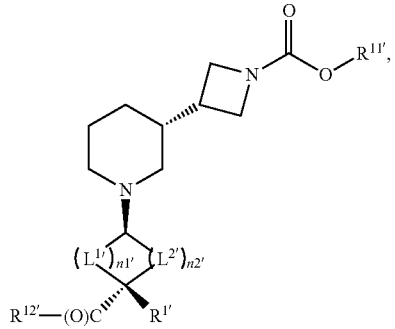

wherein $R^{11'}$ is a substituted or unsubstituted alkyl and each of n1' and n2' is 1 or 2.

Embodiment 18. The method of any one of embodiments 14 to 17, wherein the compound of formula (III) is:

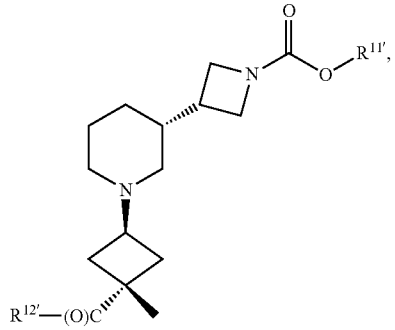

wherein $R^{11'}$ is t-butyl or benzyl.

Embodiment 19. The method of embodiment 1 or 2, wherein the CCR4 antagonist is selected from:

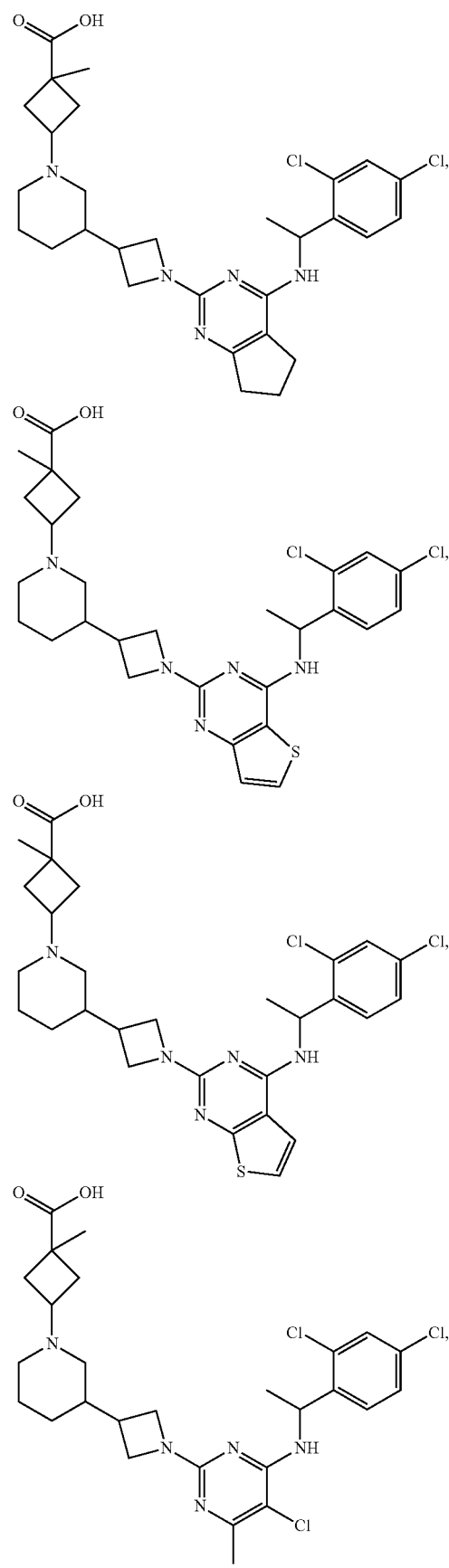

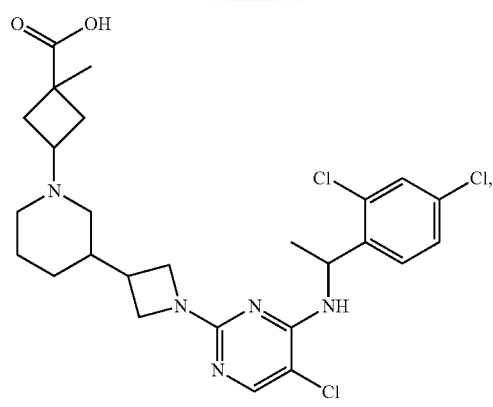
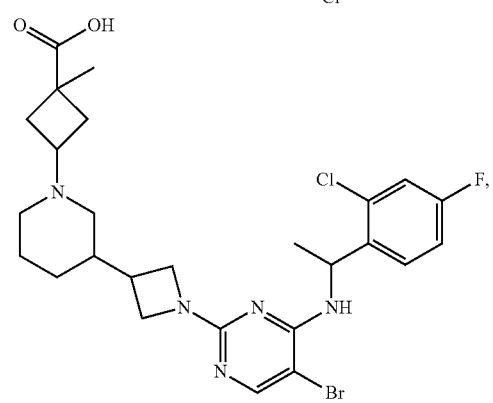
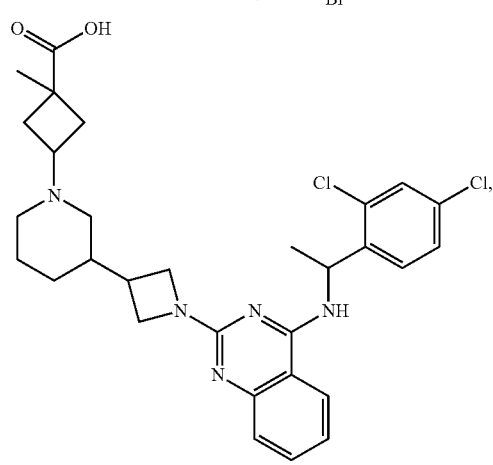
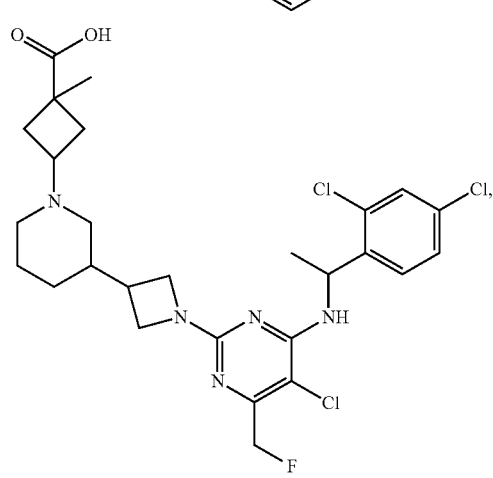
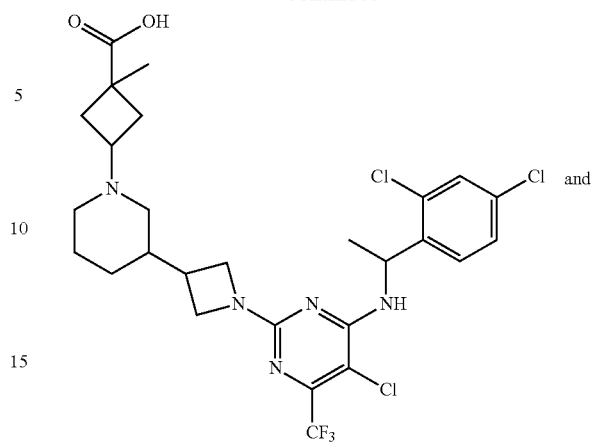
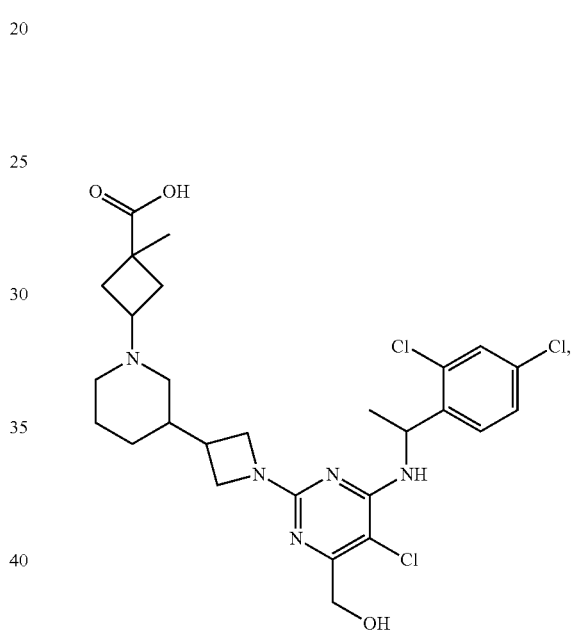
or a pharmaceutically acceptable salt or ester thereof.
Embodiment 20. The method of embodiment 1 or 2, wherein the CCR4 antagonist is selected from:
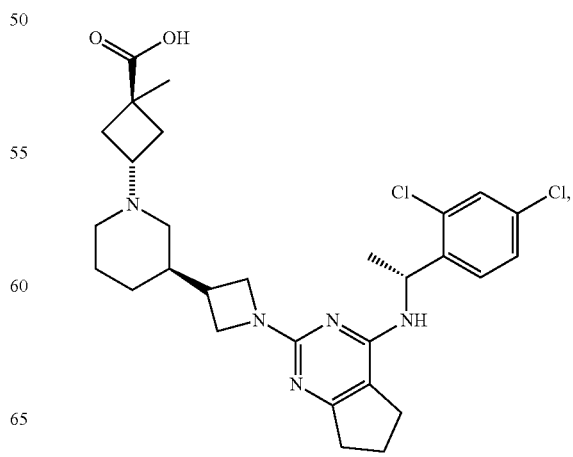

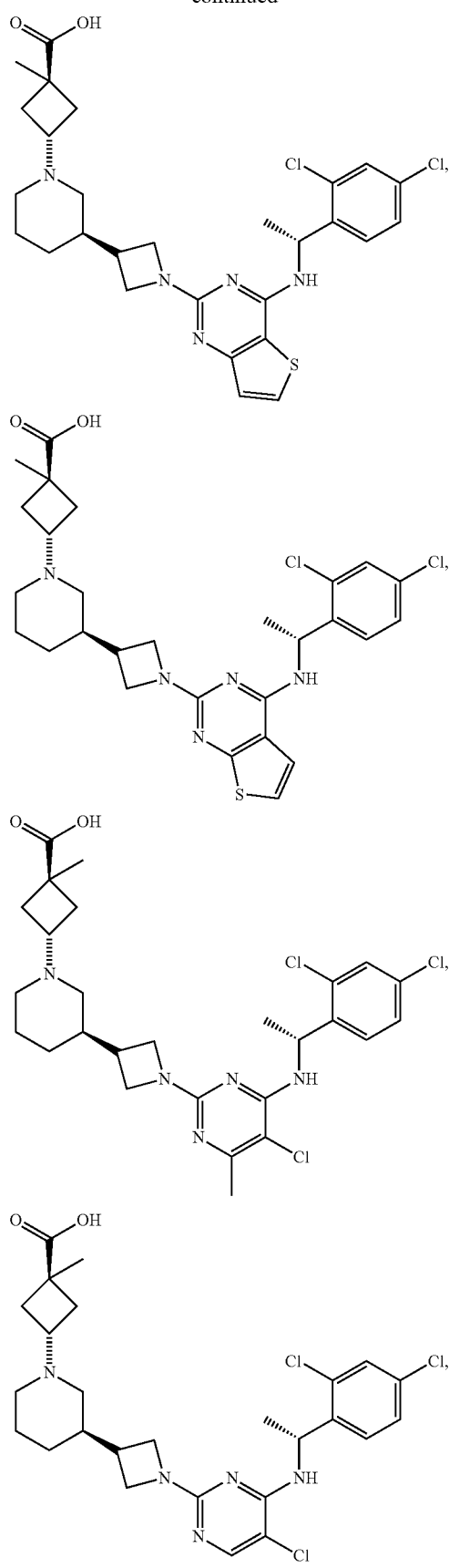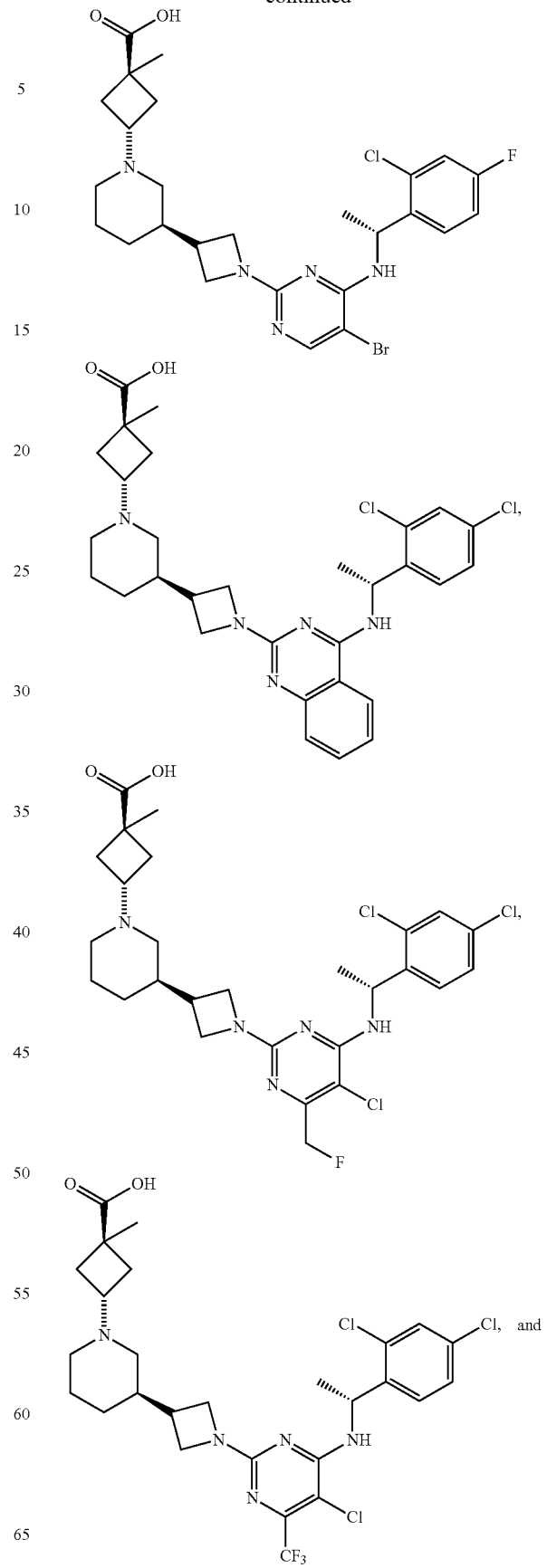

-continued

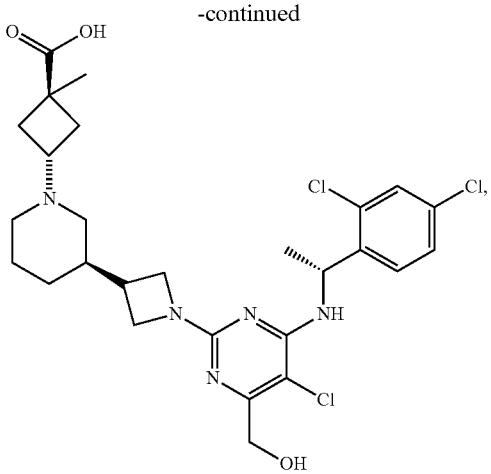

or a pharmaceutically acceptable salt or ester thereof

What is claimed is:

1. A method of synthesis of a compound of formula (III), said method comprising reacting a compound of formula (I) with a compound of formula (II) in the presence of a carboxylic acid directed reducing agent, wherein the carboxylic acid directed reducing agent is a 1,4-dihydropyridine to form the compound of formula (III):

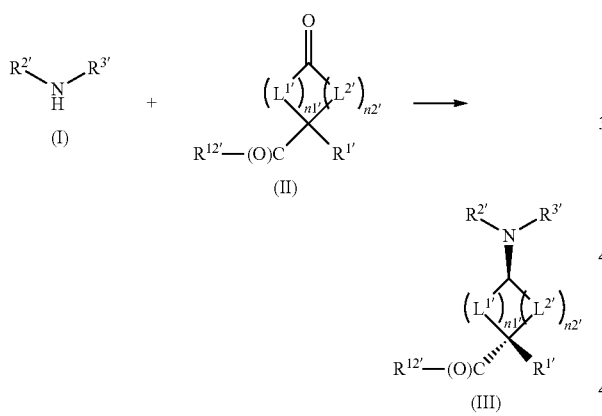

wherein:
n1' and n2' are each independently an integer from 0 to 5, wherein the sum of n1' and n2' is at least 1 and not more than 6;
$L^{1'}$ is $C(R^{4'})_2$;
$L^{2'}$ is $C(R^{5'})_2$;
$R^{1'}$ is hydrogen or a substituted or unsubstituted $C_1$-$C_4$ alkyl;
$R^{2'}$ and $R^{3'}$ are joined to form a substituted piperidinyl, wherein the piperidinyl is substituted with a substituted or unsubstituted nitrogen-containing 4-membered to 6-membered heterocycloalkyl or a substituted or unsubstituted aryl;
$R^{4'}$ is hydrogen or a substituted or unsubstituted $C_1$-$C_4$ alkyl;
$R^{5'}$ is hydrogen or a substituted or unsubstituted $C_1$-$C_4$ alkyl; and
$R^{12'}$ is —OH.

2. The method of claim 1, wherein the compound of formula (III) is in at least 80% trans isomerically pure form.

3. The method of claim 1, wherein the carboxylic acid directed reducing agent is the 1,4-dihydropyridine of formula (IV):

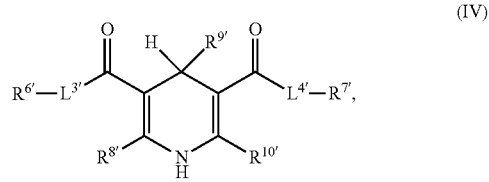

wherein:
$L^{3'}$ and $L^{4'}$ are independently —O—;
$R^{6'}$ is a substituted or unsubstituted $C_1$-$C_4$ alkyl;
$R^{7'}$ is a substituted or unsubstituted $C_1$-$C_4$ alkyl;
$R^{8'}$ is a substituted or unsubstituted $C_1$-$C_4$ alkyl;
$R^{9'}$ is hydrogen; and
$R^{10'}$ is a substituted or unsubstituted $C_1$-$C_4$ alkyl.

4. The method of claim 1, wherein n1' and n2' are independently 1 or 2 and $R^{1'}$ is a substituted or unsubstituted $C_1$-$C_2$ alkyl.

5. The method of claim 4, wherein n1' and n2' are independently 1 and $L^{1'}$ and $L^{2'}$ are independently substituted or unsubstituted $C_1$-$C_2$ alkyl.

6. The method of claim 1, wherein the compound of formula (I) is:

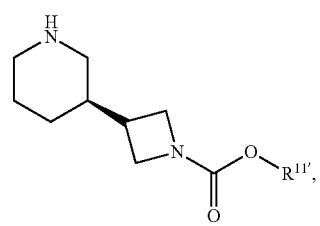

wherein:
$R^{11'}$ is a substituted or unsubstituted alkyl or a substituted or unsubstituted aryl.

7. The method of claim 6 wherein $R^{11'}$ is a substituted or unsubstituted $C_1$-$C_4$ alkyl.

8. The method of claim 1, wherein the compound of formula III is:

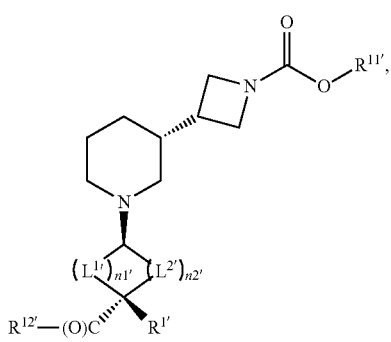

wherein $R^{11'}$ is a substituted or unsubstituted alkyl and each of n1' and n2' is 1 or 2.

9. The method of claim 8, wherein the compound of formula (III) is:

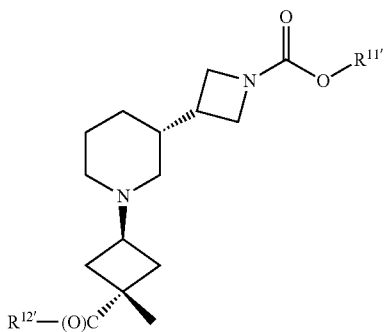

wherein $R^{11'}$ is t-butyl or benzyl.

10. The method of claim 1, wherein $R^{2'}$ and $R^{3'}$ are joined to form a substituted piperidinyl, wherein the piperidinyl is substituted with a substituted or unsubstituted nitrogen-containing 6-membered heterocycloalkyl.

11. The method of claim 10, wherein the nitrogen-containing 6-membered heterocycloalkyl is selected from substituted or unsubstituted tetrahydropyridinyl, substituted or unsubstituted piperidinyl, substituted or unsubstituted morpholinyl and substituted or unsubstituted piperazinyl.

12. The method of claim 11, wherein the nitrogen-containing 6-membered heterocycloalkyl is a substituted piperidinyl.

13. The method of claim 12, wherein the nitrogen-containing 6-membered heterocycloalkyl is piperidinyl substituted with —COOR$^{11'}$ and $R^{11}$ is a substituted or unsubstituted $C_1$-$C_4$ alkyl.

* * * * *